(12) United States Patent
Singh et al.

(10) Patent No.: US 7,645,767 B2
(45) Date of Patent: Jan. 12, 2010

(54) PHARMACEUTICAL COMPOSITIONS FOR TREATING CHRONIC PAIN AND PAIN ASSOCIATED WITH NEUROPATHY

(75) Inventors: Chandra Ulagaraj Singh, San Antonio, TX (US); David Lloyd Woody, New Braunfels, TX (US); Jagaveerabhadra Rao Nulu, Austin, TX (US)

(73) Assignee: Trinity Laboratories, Inc., San Antonio, TX (US)

( * ) Notice: Subject to any disclaimer, the term of this patent is extended or adjusted under 35 U.S.C. 154(b) by 0 days.

(21) Appl. No.: 11/892,422

(22) Filed: Aug. 22, 2007

(65) Prior Publication Data

US 2008/0058362 A1 Mar. 6, 2008

Related U.S. Application Data

(60) Provisional application No. 60/841,225, filed on Aug. 31, 2006.

(51) Int. Cl.
*A61K 31/44* (2006.01)

(52) U.S. Cl. ...................... 514/282; 514/281

(58) Field of Classification Search .................. 514/282
See application file for complete search history.

(56) References Cited

U.S. PATENT DOCUMENTS

| | | | |
|---|---|---|---|
| 4,486,450 A | 12/1984 | Bernstein | |
| 4,493,848 A | 1/1985 | LaHann | |
| 4,564,633 A | 1/1986 | LaHann | |
| 4,599,342 A | 7/1986 | LaHann | |
| 4,602,909 A | 7/1986 | Csillik | |
| 4,656,177 A | 4/1987 | Sunshine | |
| 4,769,372 A | 9/1988 | Kreek | |
| 4,777,174 A | 10/1988 | Sunshine | |
| 4,812,446 A | 3/1989 | Brand | |
| 4,997,853 A | 3/1991 | Bernstein | |
| 5,021,450 A * | 6/1991 | Blumberg | ............... 514/453 |
| 5,099,030 A | 3/1992 | Gardner | |
| 5,134,166 A | 7/1992 | Bernstein | |
| 5,178,879 A | 1/1993 | Adekunle | |
| 5,248,678 A | 9/1993 | Costa | |
| 5,290,816 A | 3/1994 | Blumberg | |
| 5,336,691 A | 8/1994 | Raffa | |
| 5,352,683 A | 10/1994 | Mayer | |
| 5,403,868 A | 4/1995 | Reid | |
| 5,516,803 A | 5/1996 | Raffa | |
| 5,560,910 A | 10/1996 | Crandall | |
| 5,578,645 A | 11/1996 | Askanazi | |
| 5,741,510 A | 4/1998 | Rolf | |
| 5,762,963 A | 6/1998 | Byas-Smith | |
| 5,827,886 A | 10/1998 | Hersh | |
| 5,889,041 A | 3/1999 | Anzalone | |
| 5,910,512 A | 6/1999 | Conant | |
| 5,916,565 A | 6/1999 | Rose | |
| 5,919,826 A | 7/1999 | Caruso | |
| 5,962,532 A | 10/1999 | Campbell | |
| 6,054,451 A | 4/2000 | Caruso | |
| 6,277,398 B1 | 8/2001 | Caruso | |
| 6,326,374 B1 | 12/2001 | Magnus | |
| 6,348,501 B1 | 2/2002 | Holt | |
| 6,537,991 B1 | 3/2003 | Shaw | |
| 6,573,302 B1 | 6/2003 | Holt | |
| 6,593,370 B2 | 7/2003 | Tamura | |
| 6,900,189 B2 | 5/2005 | Raffa | |
| 7,144,587 B2 | 12/2006 | Oshlack | |
| 7,157,103 B2 | 1/2007 | Sackler | |
| 2001/0002406 A1 | 5/2001 | Robbins | |
| 2001/0036943 A1 | 11/2001 | Coe | |
| 2002/0035105 A1 | 3/2002 | Caruso | |
| 2002/0058048 A1 | 5/2002 | Tamura | |
| 2002/0058673 A1 | 5/2002 | Kaiko | |
| 2003/0064122 A1 | 4/2003 | Goldberg | |
| 2003/0082249 A1 | 5/2003 | Gordon | |
| 2003/0125347 A1 | 7/2003 | Anderson | |
| 2003/0133995 A1 | 7/2003 | Mellott | |
| 2004/0087558 A1 | 5/2004 | Zeldis | |
| 2004/0102525 A1 | 5/2004 | Kozachuk | |
| 2004/0146590 A1 | 7/2004 | Iadarola | |
| 2004/0224037 A1 | 11/2004 | Romero-Matos | |
| 2005/0019436 A1 | 1/2005 | Burch | |
| 2005/0026956 A1 * | 2/2005 | Carliss et al. | ............... 514/326 |
| 2005/0038062 A1 | 2/2005 | Burns | |
| 2005/0203142 A1 | 9/2005 | Zeldis | |
| 2006/0233901 A1 * | 10/2006 | Jamieson et al. | ............. 424/760 |
| 2006/0235022 A1 | 10/2006 | Sun | |
| 2006/0240128 A1 | 10/2006 | Schlagheck | |
| 2006/0258669 A1 | 11/2006 | Kyle | |
| 2007/0014732 A1 | 1/2007 | Sackler | |
| 2007/0027159 A1 | 2/2007 | Kyle | |
| 2007/0054843 A1 | 3/2007 | Yeomans | |

FOREIGN PATENT DOCUMENTS

| WO | WO 01/47508 | 7/2001 |
|---|---|---|
| WO | WO 01/91736 | 12/2001 |
| WO | WO 2005/042498 | 5/2005 |
| WO | WO 2005/046687 | 5/2005 |

* cited by examiner

*Primary Examiner*—Sreeni Padmanabhan
*Assistant Examiner*—Timothy E Betton
(74) *Attorney, Agent, or Firm*—Reed Smith LLP; Nanda P. B. A. Kumar

(57) ABSTRACT

Chronic pain is alleviated in a mammal suffering there from by administering to the mammal a chronic pain alleviating amount of a nontoxic N-methyl-D-aspartate receptor antagonist such as dextromethorphan, dextrorphan, ketamine or pharmaceutically acceptable salt thereof, in combination with a μ-opiate analgesic such as tramadol or an analogously acting molecular entity, and a capsaicin or an ester of capsaicin, and optionally in sustained release dosage form.

18 Claims, 3 Drawing Sheets

PHARMACEUTICAL COMPOSITIONS FOR TREATING CHRONIC PAIN AND PAIN ASSOCIATED WITH NEUROPATHY

CROSS-REFERENCE TO RELATED APPLICATIONS

This application claims the benefit of Provisional Patent Application Ser. No. 60/841,225, filed Aug. 31, 2006 by the present inventors.

FEDERALLY SPONSORED RESEARCH

None

SEQUENCE LISTING OR PROGRAM

None

FIELD OF INVENTION

This invention relates to the treatment of pain. More specifically it relates to the treatment of pain using capsaicin. Even more specifically it relates to the treatment of pain using a nontoxic N-methyl-D-aspartate receptor antagonist such as dextromethorphan, dextrorphan, ketamine or pharmaceutically acceptable salt thereof, in combination with a μ-opiate analgesic such as tramadol or an analogously acting molecular entity, and a capsaicin or an ester of capsaicin, and optionally in sustained release dosage form.

BACKGROUND OF THE INVENTION

Chronic pain is persistent pain which has long outlasted the onset of any known or suspected physical cause or is due to an irreparable insult to, or degenerative process within some structure of the body of a human or other mammal. The pain must also be of protracted duration with little or no incremental improvement, usually having a duration greater than 6 months. It can occur after a known injury or disease or it can occur without any known physical cause whatsoever. Moreover, it can be accompanied by known tissue pathology, such as chronic inflammation that occurs in some types of arthritis, or it can occur long after the healing of the injured tissue that is suspected or known to be the cause of the chronic pain. Chronic pain is a component of the pathology of a variety of mammalian diseases. Chronic pain can be classified into one or more of several easily recognizable and familiar types. Among these are pain related to disorders of the musculoskeletal system, visceral organs, skin and nervous system. In addition chronic pain has a psychological component. This psychological pain that arises from a physical cause can be called suffering. Suffering can drive an individual to aberrant behaviors such as drug abuse and the associated social pathology complex known as crime. Finally, suffering has been found to give rise to a vicious cycle of increasing torture for the sufferer of such intensity and duration that the quality of life is lost. It is the purpose of this invention to ameliorate to a significant degree the suffering of the victims of chronic pain.

Chronic pain can be somatogenic, neurogenic, or psychogenic in origin. Somatogenic pain can be muscular or skeletal. For example, osteoarthritis, lumbosacral back pain, posttraumatic, spinal and peripheral nervous system injury, phantom pains due to amputations and avulsions and myofascial pain are unfortunately familiar to many of us. Maladies of the viscera such as chronic pancreatitis, ulcers, and irritable bowel disease give rise to pain in large numbers of people. Ischemic events frequently cause pain as in arteriosclerosis obliterans, stroke, heart attack, and angina pectoris. Cancer is also the cause of significant pain in our society. Neurogenic pain can be due to posttraumatic and postoperative neuralgia. Neurogenic pain also can be related to degenerative neuropathies due to diabetes and can be secondary to a variety of toxic insults. Neurogenic pain can also be due to nerve entrapment, irritation or disruption, facial neuralgia, perineal neuralgia, post-amputation phantom pain, thalamic, causalgia, and reflex sympathetic dystrophy. Psychogenic pain on the other hand, is not amenable to corrective physical treatments or to pharmacological treatments that either alleviate some attribute of a pathophysiologic process. Psychogenic pain is treated instead with psychiatric interventions such as counseling and psychopharmaceuticals such as antidepressants.

Neuropathic pain is a common variety of chronic pain. It can be defined as pain that results from an abnormal functioning of the peripheral and/or central nervous system. A critical component of this abnormal functioning is an exaggerated response of pain related nerve cells either in the periphery or in the central nervous system. An example is the pain known as causalgia, wherein even a light touch to the skin is felt as an excruciating burning pain. Neuropathic pain is thought to be a consequence of damage to peripheral nerves or to regions of the central nervous system. However, abnormal functioning of pain related regions of the nervous system can also occur with chronic inflammatory conditions such as certain types of arthritis and metabolic disorders such as diabetes. Thus, many types of chronic pain related to inflammatory processes can be considered to be at least partly neuropathic pains.

The modern concept of pain treatment emphasizes the significance of prophylactic prevention of pain, as pain is more easily prevented than it is relieved. Additionally the hormonal stress responses associated with pain are considered harmful to the patient because they impair the healing process and can limit the degree of overall recovery. Therefore, if possible, hormonal responses in a chronic pain patient are preferably avoided or minimized. Pain is generally controlled by the administration of short acting analgesic agents, steroids and non-steroidal anti-inflammatory drugs. Analgesic agents include opiates, agonistic-antagonistic agents, and anti-inflammatory agents.

Opiates, a class of centrally acting compounds, are the most frequently used agents for pain control. Opiates are narcotic agonistic analgesics and are drugs derived from opium, such as morphine, codeine, and many synthetic congeners of morphine, with morphine and hydrocodone preparations being the most widely used opiates. Opiates are natural and synthetic drugs with morphine-like actions. Opiates are narcotic agonistic analgesics which produce drug dependence of the morphine type and are subject to control under Federal narcotics law and the laws of most other nations and international organizations because of their addicting properties and the subsequent destructive toll exacted on the abusers and those with any connection to them. The term "opiates" also includes opiate antagonists that are essentially devoid of agonist activity at any opiate receptor, partial agonists, and opiates with mixed actions, that is they are mixed function agonist-antagonists, which are agonists at some receptors and antagonists at other receptors.

The chemical classes of opiates with morphine like activity are the purified alkaloids of opium consisting of phenanthrenes and benzylisoquinolines, semi-synthetic derivatives of morphine, phenylpiperidine derivatives, morphinan derivatives, benzomorphan derivatives, diphenyl-heptane derivatives, and propionanilide derivatives. The principal phenanthrenes are morphine, codeine, and thebaine. The principal benzoisoquinolines are papaverine, a smooth muscle relaxant, and noscapine. Semi-synthetic derivatives of morphine include diacetylmorphine (heroin), hydromorphone, oxymorphone, hydrocodone, apomorphine, etorpine, and oxycodone. Phenylpiperidine derivatives include meperidine and its congeners diphenoxylate and loperamide, alphaprodine, anileridine hydrochloride or phosphate, and piminodine mesylate. The currently used morphinan derivative is levorphanol. The diphenyl-heptane derivatives include methadone and its congeners, and propoxyphene. Propionanilide derivatives include fentanyl citrate and its congeners sufentanil citrate and alfentanil hydrochloride. These opiate analgesics are discussed in detail in Goodman and Gilman's The Pharmacological Basis of Therapeutics, Chapter 21, "Opiate Analgesics and Antagonists", pp. 485-521 ($8^{th}$ ed. 1990), which is incorporated herein by reference.

The most commonly used pain treatment during the immediate postoperative period is the repeated administration of opiates, whether intravenously, intramuscularly, or subcutaneously. The potency of all opiates is roughly comparable and can be effective against the most severe pain with appropriate dosing at intervals. However, all of these opiates have a wide variety of side effects that can decrease their clinical utility in certain situations. The side effects associated with the use of opiates include respiratory depression, reduced cough reflex, bronchial spasms, nausea, vomiting, release of histamine, peripheral vasodilation, orthostatic hypotension, alteration of vagal nerve activity of the heart, hyperexcitability of smooth muscles (sphincters), reduction of peristaltic motility in the gastrointestinal tract and urinary retention. Opiates also stimulate the release of adrenalin, anti-diuretic hormone, cause changes in the regulation of body temperature and sleep pattern, and are liable to promote the development of tolerance and addiction.

The depressive effects on respiratory function are of special importance to the post-operative mammalian patient. During the course of major surgery under general anesthesia, a mammalian patient is typically put to sleep with anesthetic agents, is paralyzed with muscle relaxants, is intubated and placed on mechanical ventilation, and is given analgesic agents. All of these treatments have direct and indirect effects that depress respiratory drive with the net consequence that postoperatively the mammalian patient may have trouble breathing. As opiates may cause clinically significant respiratory depression, reduce the cough reflex, and cause bronchial spasms, it is necessary to very carefully and precisely control the administration of opiates to mammalian patients for pain control immediately after surgery in order to avoid impairing respiratory function. Conversely, in the event that opiates are contraindicated or are administered incorrectly the mammalian patient is deprived of effective post-operative pain control that causes unnecessary and unjustifiable suffering.

In addition to the μ-opiate receptor agonists such as morphine, other classes of analgesic agents that are commonly used include agonistic-antagonistic analgesic agents, non-steroidal anti-inflammatory drugs (NSAIDS), steroids, cyclooxygenase inhibitors, anti-depressants, minerals such as magnesium, tryptan drugs for migraines, ergotamine and related compounds for migrainous headache and dissociative psychoactive drugs. Agonistic-antagonistic analgesic agents are effective for the alleviation of moderate to severe pain, but due to their antagonistic properties, their analgesic efficacy does not increase by increasing the dosage above a certain level. Furthermore, higher doses of agonistic-antagonistic analgesic agents are often associated with unpleasant sympathomimetic side effects such as tachycardia, increase in blood pressure, seizure and psychotomimetic effects such as drug induced psychosis, hyper-aggressive behavior and agitation.

However, the risk of respiratory depression also decreases proportionately with the diminished analgesic activity of the higher doses. Agonistic-antagonistic analgesic agents with pharmacological activity similar to the morphine like opiates include pentazocine, nalbuphine, butorphanol, nalorphine, buprenorphine (a partial agonist), meptazinol, dezocine, and cyclazocine.

The NSAIDs include the salicylates such as salicylamide and acetylsalicylic acid (aspirin). Non-aspirin NSAIDs include para-aminophenol derivatives such as phenacetin, the pyrazole derivatives such as antipyrine, aminopyrine, dypyrone, nefenamic acid, indomethacin, methimazole, paracetamol, diclophenac sodium/potassium, ibuprofen, naproxen, and ketorolac tromethamine, all of which can be combined with opiates or used alone to alleviate milder pain. The mechanism of action of NSAIDs is by direct action at the site of tissue injury. NSAIDs peripherally inhibit cyclooxygenases (COX), the enzymes responsible for providing an activated substrate molecules for the synthesis of prostaglandins, which are a group of short-acting mediators of inflammation. The maximal analgesic effect of a standard 325 mg dose of aspirin or of NSAIDs is adjusted to provide the level of pain relief comparable to that achieved by the administration of five milligrams of morphine administered intramuscularly.

The analgesic acetaminophen is often categorized as a NSAID even though the compound does not exhibit significant anti-inflammatory activity. Unless otherwise indicated, acetaminophen will be referred to herein as a NSAID.

It is unfortunate that opiates, including the accepted 'socially accepted opiate' alcohol, have the very significant drawback of being terribly addictive when administered ad libidem to an individual with the wrong combination of genetic and/or psychological susceptibility to addiction, with all of the attendant social, psychological and physical problems that are associated with drug abuse. By stating this we must not misinterpret or misuse this knowledge as providing some justification for moralistic or legislative punitive action. Opiates most definitely have a place in the therapeutic armamentarium, but only when administered and used wisely.

Another difficulty that has recently been gaining increasing attention is the negative side effects of non-steroidal anti-inflammatory agents. Side effects of NSAIDs include gastrointestinal irritation, clotting difficulty and secondary anemia, bronchospastic effects in asthmatic mammalian patients, and tinnitus. The overuse of NSAIDS is in fact be largely due to the inappropriate under treatment of pain in individuals who for whatever reason do not use more effective drugs that operate on other parts of the pain pathway. The analgesic agents are all used in similar ways to treat chronic pain in mammals. However, mammals will develop tolerance to the analgesic effect and develop psychological and physical dependencies on these agents, especially the opiates, thereby reducing the effectiveness of the pain treatment and exacerbating the suffering of the patient. The long term administration of narcotic analgesics to patients suffering from various types of chronic pain such as causalgia, hyperesthesia, sympathetic dystrophy, phantom limb syndrome, denervation, etc., is subject to a number of serious drawbacks including the development of opiate tolerance and/or dependence, severe constipation, and so forth.

In addition, the present invention can avoid the liability of gastrointestinal and liver toxicity by omitting acetaminophen, aspirin and other NSAID's. Acetaminophen toxicity is well known and represents a significant drawback of all formulations that contain it. The limiting dose of acetaminophen is on the order of 2 grams per day. It has also been determined that intentional overdose of acetaminophen is the second most common method of committing suicide in Europe. Thus, reducing or eliminating exposure to acetaminophen is of significant importance.

Physical dependence or drug addiction to narcotic drugs has been traditionally treated by drug withdrawal through withholding the opiate from the drug dependent individual, gradually decreasing the amount of opiate taken by the individual, administering an opiate antagonistic drug, or substituting another drug, such as methadone, buprenorphine, or methadyl acetate for the opiate to ameliorate the physical need for the opiate. In addition the psychology of the person is treated through therapeutic interventions such as individual and group therapies. When an opiate is discontinued withdrawal symptoms appear. The character and severity of the withdrawal symptoms are dependent upon such factors as the particular opiate being withdrawn, the daily dose of the opiate, the duration of use of the opiate and the health of the drug dependent individual. The physical and psychological pain associated withdrawal symptoms can be quite severe.

For example, the withdrawal of morphine, heroin, or other µ-opiate agonists with similar durations of action from an individual dependent upon the opiate gives rise to lacrimation, rhinorrhea, yawning, and sweating 8 to 12 hours after the last dose of the opiate. As withdrawal progresses, the individual develops dilated pupils, anorexia, gooseflesh, restlessness, irritability, and tremor. At the peak intensity of withdrawal, which is 48 to 72 hours for morphine and heroin, the individual suffers from increasing irritability, insomnia, marked anorexia, violent yawning, severe sneezing, lacrimation, coryzia, feelings of weakness, depression, increases of blood pressure and heart rate, nausea and severe vomiting, intestinal spasm, and diarrhea. The individual commonly experiences chills alternating with hot flushes and sweating, as well as abdominal cramps, muscle spasms and kicking movements, and perceives pains in the bones and muscles of the back and extremities, exhibits leukocytosis and an exaggerated respiratory response to carbon dioxide which causes yawning. Typically the individual does not eat or drink adequately which, when combined with the vomiting, sweating, and diarrhea, results in weight loss, dehydration, and ketosis. The withdrawal symptoms from morphine and heroin usually disappear in 7 to 10 days, but the drug dependent individual suffers greatly during the withdrawal period. If an opiate antagonistic drug is administered to the individual, such as naloxone, withdrawal symptoms develop within a few minutes after parenteral administration and reach peak intensity within 30 minutes, with a more severe withdrawal than that caused by simply withholding the opiate. Withdrawal of other morphine like opiates will produce the same or similar withdrawal symptoms, with the intensity of the symptoms dependent upon the duration of action of the morphine opiate.

The drug withdrawal symptoms and the pain associated with them will be alleviated if a suitable opiate is given to the individual. Unfortunately this could result in the individual merely substituting one opiate dependency for another. In the case of individuals dependent upon opiates such as morphine or heroin, methadone, an opiate with morphine-like activity, is given to the drug dependent individual on a daily basis in a rigidly controlled regimen. The methadone suppresses the opiate withdrawal symptoms and diminishes the euphoric effects of all opiates, but if the methadone is abruptly withdrawn, withdrawal symptoms similar to those caused by morphine restriction will appear, albeit of lower intensity but which are of longer duration.

An alternative approach to pain treatment employing the analgesic agents described above was tried in which an aromatic amino acid, tryptophan, was administered to persons undergoing third molar surgery to alleviate the pain and reduce or eliminate the consumption of other analgesics. The rationale was that serotonin, a neurotransmitter and a component of the serotonergic pain suppression pathway, is synthesized from tryptophan after the tryptophan is transported across the blood-brain barrier. Tryptophan is a precursor of serotonin and it was assumed that it would have analgesic effects. It was found however that tryptophan had no effect on post-operative pain or on the consumption of other analgesics (Ekblom, A., et al, "Tryptophan supplementation does not affect post-operative pain intensity or consumption of analgesics" Pain 1991; 44:249-254).

Other treatments include the use of antidepressants, specifically, the tricyclic antidepressants (TCA's), such as amytriptiline. These relieve pain by altering levels of serotonin in the body. The antineuralgic properties of TCA's were shown to be independent from their antidepressant properties. TCA's are associated with a number of adverse side effects such as sedation, orthostatic hypotension, dry mouth, urinary retention, constipation, and weight gain. These side effects are more pronounced in the elderly. TCA's should be used with caution in the elderly, patients with heart disease, narrow angle glaucoma, and prostatism. Another class of antidepressants, the selective serotonin reuptake inhibitors (SSRI's), may also be used. In general, the SSRI's have not been found to be as effective as the TCA's for the treatment of neuropathic pain, but are better tolerated. The side effects of the SSRI's include sweating, stomach upset, somnolence, dizziness, decreased libido, and ejaculatory disturbances.

Changes in serotonin transport function and in neuroreceptor loading that occur over the course of antidepressant use create a dependence on the drug that takes some time to be eliminated even when the drug is no longer needed to stabilize depression. Adverse effects that can arise from reducing the drug dose have been given a name: SSRI Withdrawal Syndrome or SSRI Discontinuation Syndrome (Bull 2002; Barbui 2000; Skaehill 1997). To avoid this syndrome, very gradual withdrawal—as little as 5% dosage decline per week-has been recommended; rarely are the drugs withdrawn at a rate of more than 20% per week. Unfortunately, many patients are hesitant to spend this much time withdrawing from the drug, and many physicians do not recommend such gradual dosage decline, believing that the majority of the patients will do well with relatively rapid withdrawal, so SSRI Withdrawal Syndrome can readily occur; some patients may experience the symptoms even with very gradual tapering of dosage.

U.S. Pat. No. 5,578,645 teaches the method for treating acute or chronic pain in a mammal comprising the administration of a therapeutically effective amount of an analgesic solution composed of at least one branched chain amino acid selected from the group consisting of leucine, isoleucine, and valine, or administering a therapeutically effective amount of an analgesic solution comprising an analgesic agent selected from the group consisting of an opiate, an agonistic-antagonistic agent, and an anti-inflammatory agent, and at least one branched chain amino acid selected from the group consisting of leucine, isoleucine, and valine.

U.S. Pat. No. 4,769,372 describes a method for treating chronic pain or chronic cough in a patient while preventing or alleviating the development of constipation or other symptoms of intestinal hypomotility wherein an opiate analgesic or antitussive such as morphine, meperidine, oxycodone, hydromorphone, codeine and hydrocodone is administered to the patient together with an opiate antagonist such as naloxone, naloxone glucuronide or nalmefene glucuronide. However successful this therapeutic combination may be in inhibiting the development of constipation or other symptoms of intestinal hypomotility, it does not address the problems of tolerance and/or dependence that are associated with the long term administration of narcotic analgesics.

Other approaches to the treatment of chronic pain and neuropathic pain have included the administration of a pharmaceutically acceptable acid addition salt or a protonated derivative of at least one microtubule inhibitor such as vinblastine, dexacetoxyvinblastine, vincristine, vindesine, leurosine and N-formyl-leurosine as disclosed in U.S. Pat. No. 4,602,909, (3S,4S)-7-hydroxy-$\Delta^6$-tetrahydro-cannabinol homologues and derivatives essentially free of the (3R,4R) form as disclosed in Hayes et al, Pain, 48 (1992) 391-396, Mao et al, Brain Res., 584 (1992) 18-27, 584 (1992) 28-35 and 588 (1992) 144-149 and the N-methyl-D-aspartate (NMDA) receptor antagonist, or blocker, MK801 (the compound 5-methyl-10,11-dihydro-5H-dibenzo[a,d]cyclohepten-5,10-imine) as disclosed in Mao et al, Brain Res., 576 (1992) 254-262. It was noted that MK 801 was unsuitable for use as a therapeutic due to its pronounced central nervous system neurotoxicity.

Dextromethorphan (frequently abbreviated as DM) is the common name for (+)-3-methoxy-N-methylmorphinan (FIG. 1). It is widely used as a cough suppressant, and is described in references such as Rodd (1960) and Goodman and Gilman's Pharmacological Basis of Therapeutics (full citations to articles are provided below). Briefly, DM is a non-addictive opiate comprising a dextrorotatory enantiomer (mirror image) of the morphinan ring structure that forms the molecular core of most opiates. DM acts at a class of neuronal receptors known as sigma (σ) receptors. These are often referred to as σ opiate receptors, but there is some question as to whether they are opiate receptors, so many researchers refer to them simply as σ receptors, or as high-affinity dextromethorphan receptors. They are inhibitory receptors, which means that their activation by DM or other σ agonists causes the suppression of certain types of nerve signals. Dextromethorphan also acts at another class of receptors known as N-methyl-D-aspartate (NMDA) receptors, which are one type of excitatory amino acid (EAA) receptor. Unlike its agonist activity at σ receptors, DM acts as an antagonist at NMDA receptors, which means that DM suppresses the transmission of nerve impulses mediated by NMDA receptors. Since NMDA receptors are excitatory receptors, the activity of DM as a NMDA antagonist also leads to the suppression of certain types of nerve signals, which may also be involved in some types of coughing. Due to its activity as a NMDA antagonist, DM and one of its metabolites, dextrorphan, are being actively evaluated as possible treatments for certain types of excitotoxic brain damage caused by ischemia (low blood flow) and hypoxia (inadequate oxygen supply), which are caused by events such as stroke, cardiac arrest, and asphyxia. The anti-excitotoxic activity of dextromethorphan and dextrorphan, and the blockade of NMDA receptors by these drugs, are discussed by Choi (1987), Wong et al, (1988), Steinberg et al, (1988), and U.S. Pat. No. 4,806,543. Dextromethorphan has also been reported to suppress activity at neuronal calcium channels (Carpenter et al, 1988). Dextromethorphan and the receptors it interacts with are further discussed in Tortella et al, (1989), Leander (1989), Koyuncuoglu & Saydam (1990), Ferkany et al, (1988), George et al, (1988), Prince & Feeser (1988), Feeser et al, (1988), Craviso and Musacchio (1983), and Musacchio et al, (1988).

DM disappears fairly rapidly from the bloodstream (See for example Vetticaden et al, 1989 and Ramachander et al, 1977). DM is converted in the liver to two metabolites called dextrorphan and 3-methoxymorphinan, by an enzymatic process called O-demethylation. In this process, one of the two pendant methyl groups is replaced by hydrogen. If the second methyl group is removed, the resulting metabolite is called 5-hydroxymorphinan. Dextrorphan and 5-hydroxymorphinan are covalently bonded to other compounds in the liver. The conjugation is primarily with glucuronic acid or sulfur-containing compounds such as glutathione. These glucuronide or sulfate conjugates are eliminated fairly quickly from the body in the urine. This enzyme is usually referred to as debrisoquin hydroxylase, since it was discovered a number of years ago to hydroxylate debrisoquin. It is also referred to in various articles as P450-DB or P450-2D6. It apparently is identical to an enzyme called sparteine monooxygenase, which was shown years ago to metabolize sparteine. It was not realized until recently that a single isozyme appears to be primarily responsible for the oxidation of debrisoquin and sparteine, as well as dextromethorphan and various other substrates. Debrisoquin hydroxylase belongs to a family of enzymes known as "cytochrome P-450" enzymes, or "cytochrome oxidase" enzymes. Monooxygenation of chemical materials has been ascribed to cytochromes P450 (P450). These hemoprotein containing monooxygenase enzymes displaying a reduced carbon monoxide absorption spectrum maximum near 450 nm have been shown to catalyze a variety of oxidation reactions including hydroxylation of endogenous and exogenous compounds (Jachau, 1990). A great deal of research has been conducted on the mechanisms by which P450's catalyze oxygen transfer reactions (Testa and Jenner, 1981; Guengerich, 1989 & 1992; Brosen et. al., 1990; Murray et. al., 1990; and Porter et. al., 1991).

Dextrorphan, the major metabolite of the anti-tussive dextromethorphan, and ketamine, are known NMDA receptor antagonists. Unlike MK 801 they have few, if any, neurotoxic side effects. U.S. Pat. No. 5,352,683 discloses a method for the alleviation of chronic pain in a mammal suffering there from by administration of a nontoxic N-methyl-D-aspartate receptor antagonist such as dextromethorphan, dextrorphan, ketamine or pharmaceutically acceptable salt thereof, alone or in combination with a local anesthetic and optionally in sustained release dosage form.

Tramadol has the chemical name (+/−)-trans (RR,SS)-2-[(dimethylamino)methyl]-1-(3-methoxyphenyl)cyclohexanol, and which is often erroneously referred to in literature as the cis(RS,SR) diastereomer. Tramadol is a centrally acting, binary analgesic that is neither opiate-derived, nor is it an NSAID. It is used to control moderate pain in chronic pain settings, such as osteoarthritis and post-operative analgesia, and acute pain, such as dental pain.

Tramadol is a racemate and consists of equal quantities of (+)- and (−)-enantiomers (FIG. 1). It is known that the pure enantiomers of tramadol have a differing pharmaceutical profiles and effects when compared to the racemate. The (+)-enantiomer is distinguished by an opiate-like analgesic action due its binding with the μ-opiate receptor, and both enantiomers inhibit 5-hydroxytryptamine (serotonin) and noradrenaline (norepinephrine) reuptake, which is stronger than that of racemic mixtures of tramadol, while distinct inhibition of noradrenaline reuptake is observed with the (−)-enantiomer. It has been proven for (+)- and (−)-tramadol that, depending upon the model, the two enantiomers mutually reinforce and enhance their individual actions (Raffa et al, 1993; Grond et al, 1995 and Wiebalck et al, 1998). It is obvious to conclude that the potent analgesic action of tramadol is based on this mutually dependent reinforcement of action of the enantiomers. Tramadol's major active metabolite, O-desmethyltramadol (M1), shows higher affinity for the μ-opiate receptor and has at least twice the analgesic potency of the parent drug. O-desmethyl-N-mono-desmethyltramadol (referred to as M5 in some places in the following text and in the literature) is known as one of the in vivo metabolites of tramadol (1RS, 2RS)-2-[(dimethylamino)methyl]-1-(3-methoxyphenyl) cyclohexanol (Lintz et al, 1981). M5 penetrates the blood-brain barrier to only a limited extent, as the effects on the central nervous system, for example analgesic effects, are distinctly less pronounced on intravenous administration than on intracerebroventricular administration.

Despite the fact that tramadol is chemically unrelated to the opiates adverse side effects associated with administration of tramadol are similar to those of the opiates.

Unlugenc et al, (2002) have shown that adding magnesium or ketamine to tramadol improved analgesia and patient comfort and decreased the amount of tramadol required for postoperative pain management after major abdominal surgery. Chen et al, (2002) have shown that in the acute thermal or chemical pain model, ketamine is not effective and the net effect of ketamine and tramadol in combination was simply additive after systemic administration. However, the co-administration produced synergistic antinociception in the chemical-induced persistent pain model.

Capsaicin is a natural constituent in pungent red chili peppers. Depending on the concentration used and the mode of application, capsaicin can selectively activate, desensitize, or exert a neurotoxic effect on small diameter sensory afferent nerves while leaving larger diameter afferents unaffected (Holzer, 1991; Winter et al, 1995). Sensory neuron activation occurs due to interaction with a ligand-gated nonselective cation channel termed the vanilloid receptor (VR-1) (Caterina et al, 1997), and receptor occupancy triggers $Na^+$ and $Ca^{2+}$ ion influx, action potential firing, and the consequent burning sensation associated with spicy food or capsaicin-induced pain. VR1 receptors are present on both C and Aδ fibers, and can be activated by capsaicin and its analogs, heat, acidification, and lipid metabolites (Tominaga et al, 1998; Caterina and Julius, 2001). Desensitization occurs with repeated administration of capsaicin, is a receptor-mediated process, and involves $Ca^{2+}$- and calmodulin-dependent processes and phosphorylation of the cation channel (Winter et al, 1995; Wood and Docherty, 1997).

Capsaicin induces release of substance P and calcitonin gene-related peptide from both peripheral and central terminals of sensory neurons, and desensitization inhibits such release (Holzer, 1991); such inhibition may result from inhibition of voltage-gated $Ca^{2+}$-currents (Docherty et al, 1991; Winter et al, 1995). Desensitization leads to analgesia in rodent paradigms, with specific characteristics of analgesia depending on the dose of capsaicin, route of administration, treatment paradigm (i.e., acute or repeated administration), and age of the animal (Holzer, 1991; Winter et al, 1995). The topical skin application of capsaicin to rodents produces analgesia (Kenins, 1982; Lynn et al, 1992), but variability in outcome can occur due to the concentration, the number of applications, and the different vehicles used that can affect the rate and extent of skin penetration (Carter and Francis, 1991; McMahon et al, 1991).

Viral replication, immune regulation, and induction of various inflammatory and growth-regulatory genes require activation of a nuclear transcription factor (NF)-κ-B. Agents that can block NF-κ-B activation have potential to block downstream responses mediated through this transcription factor. Capsaicin (8-methyl-N-vanillyl-6-nonenamide) has been shown to regulate a wide variety of activities that require NF-κ-B activation (Singh 1996). The pretreatment of human myeloid ML-1a cells with capsaicin blocked TNF-mediated activation of NF-κ-B in a dose-and time-dependent manner. Capsaicin treatment of cells also blocked the degradation of I-κ-B alpha, and thus the nuclear translocation of the p65 subunit of NF-κ-B, which is essential for NF-κ-B activation. TNF-dependent promoter activity of I-κ-B alpha, which contains NF-κ-B binding sites, was also inhibited by capsaicin.

Acute intradermal injection of capsaicin to the skin in humans produces a burning sensation and flare response; the area of application becomes insensitive to mechanical and thermal stimulation, the area of flare exhibits a primary hyperalgesia to mechanical and thermal stimuli, and an area beyond the flare exhibits secondary allodynia (Simone et al, 1989; LaMotte et al, 1991). Repeated application to normal skin produces desensitization to this response and thus forms the basis of the therapeutic use of topical capsaicin in humans. Desensitization involves both physiological changes in the terminals of the sensory neuron noted above, as well as a degree of loss of sensory fiber terminals within the epidermis (Nolano et al, 1999).

Topical capsaicin preparations of 0.025 and 0.075% are available for human use, and these produce analgesia in randomized double-blind placebo-controlled studies, open label trials, and clinical reports (Watson, 1994; Rains and Bryson, 1995). Topical capsaicin produces benefit in postherpetic neuralgia (Bernstein et al, 1989; Watson et al, 1993), diabetic neuropathy (Capsaicin Study Group, 1992), postmastectomy pain syndrome (Watson and Evans, 1992; Dini et al, 1993), oral neuropathic pain, trigeminal neuralgia, and temperomandibular joint disorders (Epstein and Marcoe, 1994; Hersh et al, 1994), cluster headache (following intranasal application) (Marks et al, 1993), osteoarthritis (McCarthy and McCarthy, 1992), and dermatological and cutaneous conditions (Hautkappe et al, 1998). Whereas pain relief is widely observed in these studies, the degree of relief is usually modest, although some patients have a very good result. Topical capsaicin is generally not considered a satisfactory sole therapy for chronic pain conditions and is often considered an adjuvant to other approaches (Watson, 1994). No significant benefit was reported in chronic distal painful neuropathy (Low et al, 1995) or with human immunodeficiency virus-neuropathy (Paice et al, 2000).

The distribution and metabolism of capsaicin and/or dihydrocapsaicin has been studied in rats. Capsaicin is distributed to the brain, spinal cord, liver and blood within 20 mins. of i.v. administration. Oral doses of dihydrocapsaicin in the rat showed metabolic activity associated with its absorption into the portal vein. Capsaicin and dihydrocapsaicin are metabolized in the liver by the mixed-function oxidation system (cytochrome P-450-dependent system). It is assumed that capsaicin is excreted in urine. In rats, most of dihydrocapsaicin is known to be rapidly metabolized and excreted in the urine (Rumsfield and West, 1991).

Oral dosing of rats with capsaicin and dihydrocapsaicin results in an 85% absorption in the jejunum after 3 hours (Rumsfield and West, 1991). With respect to topical applications of capsaicin, it has been estimated that assuming 100% of a topically-applied dose is absorbed into the body, an application of 90 g capsaicin (2 tubes of cream, 0.025% capsaicin) per week would result in a daily exposure of 0.064 mg/kg capsaicin for a 50 kg person. This represents less than 10% of the dietary intake of a typical Indian or Thai diet (Rumsfield and West, 1991).

The most frequently encountered adverse effect with capsaicin is burning pain at the site of application, particularly in the first week of application. This can make it impossible to blind trials and can lead to dropout rates ranging from 33 to 67% (Watson et al, 1993; Paice et al, 2000). Another factor in compliance is the time delay before therapeutic effect is observed (at least a week, but sometimes several weeks). One approach toward minimizing adverse effects and accelerating the rate of analgesia has been to deliver a higher capsaicin concentration (5-10%) under regional anesthesia, and this produced sustained analgesia lasting 1 to 8 weeks in cases of complex regional pain syndrome and neuropathic pain (Robbins et al, 1998). When topical local anesthetics were applied with 1% topical capsaicin, no alteration in pain produced by the capsaicin was observed in healthy subjects (Fuchs et al, 1999) indicating that this cotreatment was not sufficient to block the pain induced by capsaicin.

U.S. Pat. No. 6,054,451 discloses the analgesic composition comprising (R) or (S)-5-(2-azetidinylmethoxy)-2-chloropyridine (I), or their salts; and an analgesic-potentiating amount of at least one nontoxic N-methyl-D-aspartate receptor antagonist for alleviating pain e.g. arthritic, lumbosacral or musculo-skeletal pain or pain associated with a sore throat. It has been claimed that reduced dosages of analgesic are required. U.S. Pat. No. 6,007,841 discloses analgesic composition comprises at least one narcotic agonist-antagonist analgesic and a narcotic agonist-antagonist analgesic-potentiating amount of at least one N-methyl-D-aspartate receptor antagonist.

U.S. Pat. No. 5,516,803 discloses a composition comprising a tramadol material and a nonsteroidal antiinflammatory drug, and its use. The compositions are pharmacologically useful in treating pain and tussive conditions. The compositions are also subject to less opioid side-effects such as abuse liability, tolerance, constipation and respiratory depression. Furthermore, where the components of the compositions are within certain ratios the pharmacological effects of the compositions are superadditive (synergistic).

U.S. Pat. No. 5,336,691 discloses a composition comprising a tramadol material and acetaminophen, and its use. As used herein tramadol refers to various forms of tramadol. The compositions are pharmacologically useful in treating pain and tussive conditions. The compositions are also subject to less opioid side-effects such as abuse liability, tolerance, constipation and respiratory depression. Furthermore, where the components of the compositions are within certain ratios the pharmacological effects of the compositions are superadditive (synergistic).

U.S. Pat. No. 5,919,826 discloses the analgesic effectiveness of an tramadol significantly enhanced by administering tramadol with the administration of an analgesia-enhancer which is a nontoxic NMDA receptor blocker and/or a nontoxic substance that blocks at least one major intracellular consequence of NMDA receptor activation for treating arthritis.

U.S. Pat. Nos. 4,656,177 and 4,777,174 disclose combinations of non-narcotic analgesics/nonsteroidal anti-inflammatory drugs and/or narcotic analgesics and caffeine. The compositions elicit a more potent and more rapid analgesic response than if the pain reliever is given alone.

U.S. Pat. No. 5,248,678 teaches a method of increasing the arousal an alertness of comatose patients or nea-comatose patients comprising administering to the patients effective amounts of an adenosine receptor antagonist, such as caffeine, and a GABA agonist, such as gabapentin.

U.S. Pat. No. 6,326,374 discloses compositions that comprise a GABA analog, such as gabapentin or pregabalin in combination with caffeine for the treatment of pain in mammals.

Various capsaicin compositions have been developed over the years, in particular, the psoriatic composition of U.S. Pat. No. 4,486,450, the nasal composition of U.S. Pat. No. 5,134,166, and the composition of U.S. Pat. No. 4,997,853, the anti-inflammatory composition of U.S. Pat. No. 5,560,910, the composition of U.S. Pat. No. 5,962,532, the composition for animals of U.S. Pat. No. 5,916,565, the stomach treatments of U.S. Pat. No. 5,889,041, the composition of U.S. Pat. No. 5,827,886, the patch with medication of U.S. Pat. No. 5,741,510, all of which are incorporated by reference herein.

U.S. Pat. No. 6,593,370 discloses a topical capsaicin preparation for the treatment of painful cutaneous disorders and neural dysfunction. The preparation contains a nonionic, amphoteric or cationic surfactant in an amount effective to eliminate or substantially ameliorate burning pain caused by capsaicin.

U.S. Pat. No. 6,573,302 discloses a cream comprising: a topical carrier wherein the topical carrier comprises a member selected from the group comprising lavender oil, myristal myristate, and other preservatives including, *hypericum perforatum arnica montana* capric acid; and 0.01 to 1.0 wt. % capsaicin; 2 to 10 wt. % an encapsulation agent selected from the group comprising colloidal oatmeal hydrogenated lecithin, dipotassium glycyrlhizinate and combinations thereof; esters of amino acid; a light scattering element having a particle size up to 100 nm.; and a histidine.

U.S. Pat. No. 6,348,501 discloses a lotion for treating the symptoms of arthritis using capsaicin and an analgesics, and a method for making.

U.S. Pat. No. 5,962,532 discloses methods and compositions for treating pain at a specific site with an effective concentration of capsaicin or analogues. The methods involve providing anesthesia to the site where the capsaicin or analogues thereof is to be administered, and then administering an effective concentration of capsaicin to the joint. The anesthesia can be provided directly to the site, or at remote site that causes anesthesia at the site where the capsaicin is to be administered. For example, epidural regional anesthesia can be provided to patients to which the capsaicin is to be administered at a site located from the waist down. By pretreating the site with the anesthetic, a significantly higher concentration of capsaicin can be used. Effective concentrations of capsaicin or analogues thereof range from between 0.01 and 10% by weight, preferably between 1 and 7.5% by weight, and more preferably, about 5% by weight. This provides for greater and more prolonged pain relief, for periods of time ranging from one week to several weeks. In some cases the pain relief may be more sustained because the disease that underlies the pain may improve due to a variety of factors including enhancement of physical therapy due to less pain in the soft tissues which may foster enhanced mobilization of soft tissues, tendons, and joints.

U.S. Pat. No. 5,910,512 discloses a water-based topical analgesic and method of application wherein the analgesic contains capsicum, capsicum oleoresin and/or capsaicin. This analgesic is applied to the skin to provide relief for rheumatoid arthritis, osteoarthritis, and the like.

U.S. Pat. No. 5,403,868 discloses novel capsaicin derivatives containing thio-urea, processes for the production thereof, pharmaceutical compositions containing them and use thereof as pharmaceuticals.

U.S. Pat. No. 5,178,879 discloses clear, water-washable, non-greasy gels useful for topical pain relief contain capsaicin, water, alcohol and a carboxypolymethylene emulsifier. A method of preparing the gels is also disclosed U.S. Pat. No. 5,021,450 relates to a new class of compounds having a variable spectrum of activities for capsaicin-like responses, compositions thereof, processes for preparing the same, and uses thereof. Compounds were prepared by combining phorbol related diterpenses and homovanillac acid analogs via esterification at the exocyclic hydroxy group of the diterpene. Examples of these compounds include 20-homovanillyl-mezerein and 20-homovanillyl-12-deoxyphorbol-13-phenylacetate.

U.S. Pat. No. 4,997,853 discloses a method and composition for treating superficial pain syndromes which incorporates capsaicin in a therapeutically effective amount into a pharmaceutically acceptable carrier and adding to this composition a local anesthetic such as lidocaine or benzocaine. The composition containing the anesthetic is then applied to the site of the pain. A variation on the treatment includes initial treatment with the composition containing the local anesthetic until the patient has become desensitized to the presence of capsaicin and subsequent treatment with a composition omitting the local anesthetic.

U.S. application Ser. No. 20050019436 provides compositions and methods for relieving pain at a site in a human or animal in need thereof by administering at a discrete site in a human or animal in need thereof a dose of capsaicin in an amount effective to denervate a discrete site without eliciting an effect outside the discrete location, the dose of capsaicin ranging from 1 µg to 3000 µg.

U.S. application Ser. No. 20040224037 claims a use of Capsaicin (8-methyl-n-vanillyl-6-nonenamide), its derivatives, vanilloids and capsicum extract, to combat and control HIV (humans immunodeficiency virus) and aids (acquired immunodeficiency syndrome). An evaluation of a capsicum sp consumption of a long term aids survivors group permitted a definition of more efficacious ways to administer the substance. capsaicin intravenous and by subcutaneous or intramuscular administration at low concentration implemented by using infuses, it inhibits HIV replication and stimulates the production and proliferation of lymphocytes and cells nk. Also it acts as desinfectant in macrophages, and has a power as anticancer and antioxidant agent. Moreover has the property to control and annihilate common opportunistic illnesses related to HIV due to its triple antibiotic characteristics.

U.S. application Ser. No. 20040146590 provides methods and kits for the selective ablation of pain-sensing neurons. The methods comprise administration of a vanilloid receptor agonist to a ganglion in an amount that causes death of vanilloid receptor-bearing neurons. Accordingly, the present invention provides methods of controlling pain and inflammatory disorders that involve activation of vanilloid receptor-bearing neurons.

U.S. application Ser. No. 20030133995 discloses a chemical composition for an ingestible capsaicin neutralizer to neutralize the effect of capsaicin on the oral cavity, tongue, and esophagus when capsaicin from hot peppers is ingested by a user comprised of an effective neutralizing amount of casein protein, or the salt thereof, an alkali earth metal halide, and the balance water.

U.S. application Ser. No. 20030082249 discloses a composition for use in treating or preventing mucositis, and/or xerostomia, including capsaicin or capsaicin derivative, and one or more additional compounds useful in treating mucositis and/or xerostomia, wherein the composition is provided in an oral delivery vehicle. The term capsaicin derivative and capsaicinoid as used in the disclosure are interchangeable and generally refer to capsaicin analogs. Among the capsaicinoids useful in the practice of the disclosure are capsaicin, capsaicin derivatives; dihydrocapsaicin; norhydrocapsaicin; nordihydrocapsaicin; homocapsaicin; homohydrocapsaicin; homodihydrocapsaicin; civamide (cis-capsaicin); nonivamide; NE-19550 (N-[4-hydroxy-3-methoxyphenyl)methyl]-9Z-octadecanamide) (olvanil); NE-21610 (N-[(4-(2aminoethoxy)-3-methoxyphenyl)methyl]-9Z-octadecanamide) Sandoz Pharmaceutical Corp, East Hanover, N.J.); NE-28345 (N-(9Z-octadecenyl)-3-methoxy-4-hydroxyphenylacetamide; also known as N-oleyl-homovanillamide); and their analogs and derivatives (U.S. Pat. No. 5,762,963, which is incorporated herein by reference). NE-19550, NE-21610, and NE-28345 are discussed in Dray et al, (1990).

U.S. application Ser. No. 20020058048 discloses a topical capsaicin preparation for the treatment of painful cutaneous disorders and neural dysfunction is disclosed. The preparation contains a nonionic, amphoteric or cationic surfactant in an amount effective to eliminate or substantially ameliorate burning pain caused by capsaicin.

U.S. application Ser. No. 20010002406 discloses transdermal application of capsaicin (or a capsaicin analog) in a concentration from greater than about 5% to about 10% by weight to be an extremely effective therapy for treating neuropathic pain, so long as an anesthetic, preferably by means of a transdermal patch, is administered initially to the affected area to minimize the expected side effects from subsequent capsaicin application. Analogs of capsaicin with physiological properties similar to capsaicin are known (Ton 1955). For example, resiniferatoxin is described as a capsaicin analog by Blumberg, U.S. Pat. No. 5,290,816. U.S. Pat No. 4,812,446, describes capsaicin analogs and methods for their preparation U.S. Pat. No. 7,157,103 discloses an oral dosage form comprising a therapeutically effective amount of a drug susceptible to abuse; and an effective amount of an irritant to impart an irritating sensation to an abuser upon administration of said dosage form after tampering.

U.S. application Ser. No. 20060240128 discloses a combined analgesic composition having at least one analgesic drug in an extended release form and at least one nontoxic N-methyl-D-aspartate receptor antagonist in an immediate release form, where the activity of the analgesic drug is enhanced by the at least one nontoxic N-methyl-D-aspartate receptor antagonist. Preferably, the analgesic drug is an opioid analgesic, the at least one nontoxic N-methyl-D-aspartate receptor antagonist is dextromethorphan, and the analgesic composition is substantially free of opioid antagonist.

U.S. application Ser. No. 20030064122 discloses pharmaceutical compositions which include systems to deter abuse. More specifically, the disclosure relates to compositions containing an effective amount of pharmaceutical compound and capsaicin or a capsaicinoid compound. Most specifically, the disclosure relates to a composition containing an effective amount of a pharmaceutical compound, and an amount of a capsaicin compound to deter intranasal, oral, and intravenous abuse while having little or no irritating effect when administered orally or transdermally as directed. The application claims a composition comprising: a pharmaceutically active ingredient; a capsaicinoid; wherein said composition is for subsequent formulation into a final dosage form selected from a solid oral dosage form and a transdermal dosage form; and wherein said capsaicinoid is present in an amount such that said final dosage form contains an amount effective to cause at least one response selected from coughing, sneezing, secretion, and pain when contacted with a mucosal or vascular membrane U.S. Pat. Nos. 4,493,848 and 4,564,633 disclose the derivatives of capsaicin, including short chain ester derivatives (C1-C6) of capsaicin for relieving pain.

Heretofore, there has been no recognition or appreciation that the analgesic effectiveness of tramadol can be appreciably enhanced by administration of tramadol prior to, with or following the administration of an analgesia-enhancing amount of dextromethorphan or for that matter, any other NMDA receptor antagonist and capsaicin or an ester of capsaicin.

Surprisingly, it has now been found that a combination of a non-toxic NMDA receptor antagonist such as dextromethorphan with a µ-opiate analgesic such as tramadol and capsaicin or esters of capsaicin exhibits significant palliative effects on certain types of chronic pain that result from nerve injury.

Accordingly, an object of the invention is to provide methods and compositions for the treatment of acute or chronic pain which provide effective control of pain without the harmful side effects associated with traditional analgesics, such as respiratory depression, disturbed sleep patterns, diminished appetite, seizures, and psychological and/or physical dependency. These and other objects and features of the invention will be apparent from the following description.

SUMMARY OF THE INVENTION

It is an object of the present invention to provide a method and pharmaceutical formulation, (medicament), which allows for reduced plasma concentrations of an analgesic, while still providing effective pain management.

It is a further object of the present invention to provide a method and a pharmaceutical formulation (medicament) for effectively treating patients in pain. Accordingly, the present invention provides a method that comprises administering a pharmaceutical composition comprising an analgesic combination that includes a NMDA receptor antagonist or a pharmaceutically acceptable salt thereof, capsaicin or an ester of capsaicin and a µ-opiate analgesic, which is a µ-opiate agonist, partial agonist or agonist/antagonist, or a pharmaceutically acceptable salt thereof. By this method is achieved an analgesic preparation which produces prolonged and effective pain management, while at the same time exhibits reduced side effects and decreases the liability to dependence and tolerance which the patients may experience when subjected to prolonged treatment with an opiate.

In accordance with the present invention, a NMDA receptor antagonist can be dextromethorphan, dextrorphan, ketamine, amantadine, memantine, eliprodil, ifenprodil, phencyclidine, MK-801, dizocilpine, CCPene, flupirtine, or derivatives or salts thereof.

A capsaicin can be capsaicin itself, capsaicin, civamide, homocapsaicin, nordihydrocapsaicin, dihydrocapsaicin, homodihydrocapsaicin, n-vanillyloctanamide, nonivamide, n-vanillyldecanamide, cis-capsaicin, or derivatives thereof. A µ-opiate analgesic can be any one of (1R,2R or 1S,2S)-(dimethylaminomethyl)-1-(3-methoxyphenyl)-cyclohexanol (tramadol), its N-oxide derivative ("tramadol N-oxide"), and its O-desmethyl derivative ("O-desmethyl tramadol") or mixtures, stereoisomers or racemates thereof.

The present invention further provides a method and composition for effectively treating patients in pain which avoids the toxicities associated with NSAID or acetaminophen therapy. The method comprises administering a pharmaceutical composition to a patient in need of treatment for pain, wherein the pharmaceutical composition comprises an analgesic combination comprising a NMDA antagonist or a pharmaceutically acceptable salt thereof, and a µ-opiate analgesic, which is a µ-opiate agonist, partial agonist or agonist/antagonist, or a pharmaceutically acceptable salt thereof. In accordance with the present invention, the composition can be essentially free of a NSAID or acetaminophen. Particularly relevant NSAIDs include ibuprofen, diclofenac, diflunisal, etodolac, fenoprofen, flurbiprofen, indomethacin, ketoprofen, ketorolac, mefenamic acid, meclofenamate, nabumetone, naproxen, oxaprozin or piroxicam. If the patient is separately administered a NSAID and/or acetaminophen, the amount administered is not enough to induce one or more toxicities associated with the use of the NSAID and/or acetaminophen.

Although tramadol/acetaminophen formulations containing a slew of other pharmaceutically active agents such as decongestants, antitussives, antihistamines or suspected adjuvants have been suggested in a general fashion, the particular combination of NMDA receptor antagonist, µ-opiate analgesic and capsaicin or an ester of capsaicin has not been previously recognized or appreciated. Similarly, the particular combination of NMDA receptor antagonist and µ-opiate analgesic in a composition essentially free of a NSAID and/or acetaminophen has not been recognized or appreciated.

In accordance with the present invention, the ratio of NMDA antagonist to µ-opiate agonist, partial agonist or agonist/antagonist can be from about 15:1 to 1:15, about 10:1 to 1:10, about 5:1 to 1:5, or about 1:2. The ratio of NMDA antagonist to capsaicin or an ester of capsaicin to µ-opiate agonist, partial agonist or agonist/antagonist can be from about 90:1:1 to 1:90:1 to 1:1:90.

It is yet a further object to provide a method and pharmaceutical formulation (medicament) for the effective treatment of pain in patients by augmenting the analgesic effect of a µ-opiate analgesic.

The invention is directed to the surprising and unexpected synergy obtained via the administration of a NMDA receptor antagonist together with capsaicin or an ester of capsaicin and a µ-opiate analgesic such as tramadol.

The present invention is related in part to analgesic pharmaceutical compositions comprising a NMDA receptor antagonist together with capsaicin or an ester of capsaicin and a µ-opiate analgesic. The pharmaceutical compositions can be administered intravenously, intrathecally, orally, via controlled release implant or pump, parenterally, sublingually, rectally, topically, via inhalation, etc. In other embodiments of the invention, the µ-opiate analgesic can be administered separately from the NMDA receptor antagonist and the capsaicin or an ester of capsaicin, as set forth in more detail below.

The invention allows for the use of lower doses of a µ-opiate analgesic or a NMDA receptor antagonist, (referred to as "apparent one-way synergy" herein), or lower doses of both drugs (referred to as "two-way synergy" herein) than would normally be required when either drug is used alone. By using lower amounts of either or both drugs, the side effects associated with effective pain management in humans and other species are significantly reduced.

In certain preferred embodiments, the invention is directed in part to synergistic combinations of dextromethorphan or other NMDA receptor antagonist in an amount sufficient to render a therapeutic effect together with capsaicin or an ester of capsaicin and a µ-opiate analgesic, such that an analgesic effect is attained which is at least about 5 (and preferably at least about 10) times greater than that obtained with the dose of µ-opiate analgesic alone. In certain embodiments, the synergistic combination provides an analgesic effect which is up to about 30 to 40 times greater than that obtained with the dose of μ-opiate analgesic alone. In such embodiments, the synergistic combinations display what is referred to herein as an "apparent mutual synergy", meaning that the dose of NMDA antagonist and capsaicin or an ester of capsaicin synergistically potentiates the effect of the μ-opiate analgesic and the dose of μ-opiate analgesic appears to potentiate the effect of the NMDA antagonist and the capsaicin or an ester of capsaicin.

The combination of NMDA antagonist, capsaicin or an ester of capsaicin and μ-opiate analgesic can be administered in a single dosage form. Alternatively the combination can be administered separately, preferably concomitantly.

In certain preferred embodiments, the synergism exhibited between the three types of drugs, is such that the dosage of opiate analgesic would be sub-therapeutic if administered without the dosage of the NMDA antagonist. Similarly, in certain preferred embodiments wherein the pharmaceutical composition comprises a combination of NMDA antagonist and μ-opiate analgesic and is essentially free of a NSAID or acetaminophen, the dosage of opiate analgesic would be sub-therapeutic if administered without the dosage of the NMDA antagonist. In other preferred embodiments, the present invention relates to a pharmaceutical composition comprising an analgesically effective dose of μ-opiate analgesic together with a dose of a NMDA antagonist and capsaicin or an ester of capsaicin effective to augment the analgesic effect of the μ-opiate analgesic, or a composition essentially free of a NSAID or acetaminophen and comprising an analgesically effective dose of μ-opiate analgesic together with a dose of a NMDA antagonist effective to augment the analgesic effect of the μ-opiate analgesic It is believed that in actuality these combinations exhibit two-way synergism, meaning that the NMDA antagonist and the capsaicin or an ester of capsaicin potentiate the effect of the μ-opiate analgesic, and the μ-opiate analgesic, potentiates the effect of the NMDA antagonist and the capsaicin or an ester of capsaicin. Thus, other embodiments of the invention relate to combinations of NMDA antagonist, capsaicin or an ester of capsaicin and μ-opiate analgesic where the dose of each drug is reduced due to the synergism demonstrated between the drugs, and the analgesia derived from the combination of drugs in reduced doses is surprisingly and strongly enhanced. The two-way synergism is not always readily apparent in actual dosages due to the potency ratio of the μ-opiate analgesic to the NMDA antagonist and capsaicin or an ester of capsaicin. By this we mean that the μ-opiate generally displays unexpectedly enhanced analgesic potency.

In certain preferred embodiments, the invention is directed to pharmaceutical formulations comprising a NMDA antagonist such as dextromethorphan, capsaicin or an ester of capsaicin in an amount sufficient to render a therapeutic effect, and a therapeutically effective or sub-therapeutic amount of an μ-opiate analgesic. Preferably, the μ-opiate analgesic is selected from the group consisting of tramadol, its metabolites thereof, salts thereof, and complexes thereof.

In certain preferred embodiments, the invention is directed to pharmaceutical formulations comprising a NMDA antagonist such as dextromethorphan and capsaicin or an ester of capsaicin in an amount sufficient to render a therapeutic effect together with a therapeutically effective or sub-therapeutic amount of a μ-opiate analgesic. Preferably, the μ-opiate analgesic is selected from the group consisting of tramadol and/or its salts thereof, and mixtures of any of the foregoing.

In certain preferred embodiments, the invention is directed to pharmaceutical formulations comprising a NMDA antagonist such as dextromethorphan and capsaicin or an ester of capsaicin in an amount sufficient to render a therapeutic effect together with a dose of a μ-opiate analgesic that is analgesic if administered without the NMDA antagonist and the capsaicin or an ester of capsaicin. Preferably, the μ-opiate analgesic is tramadol. The dose of tramadol is preferably from about 30 to about 400 mg.

The invention further relates to a method of effectively treating pain in mammals or humans, comprising administration to a human or mammalian patient a therapeutically effective amount of a NMDA antagonist and capsaicin or an ester of capsaicin together with a dose of an μ-opiate analgesic, such that the combination provides an analgesic effect which is at least about 5, and preferably at least about 10, times greater than that obtained with the dose of μ-opiate analgesic alone. In certain embodiments, the synergistic combination provides an analgesic effect which is up to about 30 to 40 times greater than that obtained with the dose of opiate analgesic alone.

In certain preferred embodiments, the doses of the NMDA antagonist, capsaicin or an ester of capsaicin and the μ-opiate analgesic are administered orally. In further preferred embodiments the doses of the NMDA antagonist, capsaicin or an ester of capsaicin and the μ-opiate analgesic are administered in a single oral dosage form. In certain preferred embodiments, the dose of opiate analgesic would be sub-therapeutic if administered without the dose of the NMDA antagonist and the capsaicin or an ester of capsaicin. In other preferred embodiments, the dose of μ-opiate analgesic is effective to provide analgesia alone, but the dose of μ-opiate provides at least a five fold greater analgesic effect than typically obtained with that dose of μ-opiate alone.

The invention further relates to the use of a pharmaceutical combination of a NMDA antagonist(s) together with a μ-opiate analgesic and capsaicin or an ester of capsaicin to provide effective pain management in humans and other mammals.

The invention further relates to the use of a NMDA antagonist in the manufacture of a pharmaceutical preparation containing a NMDA antagonist, capsaicin or an ester of capsaicin and a μ-opiate analgesic for the treatment of pain.

The invention further relates to the use of a μ-opiate analgesic such as tramadol in the manufacture of a pharmaceutical preparation containing a NMDA antagonist, capsaicin or an ester of capsaicin, and an opiate analgesic for the treatment of pain of chronic, intermittent or acute nature.

The invention further relates to the use of capsaicin or an ester of capsaicin or its analog in the manufacture of a pharmaceutical preparation containing a NMDA antagonist, capsaicin or an ester of capsaicin, an opiate analgesic for the treatment of pain of chronic, intermittent or acute nature.

The invention is also directed to a method for providing effective pain management in humans, comprising administration of either an analgesically effective or sub-therapeutic amount of a μ-opiate analgesic such as tramadol, administration of an effective amount of capsaicin or an ester of capsaicin in an amount effective to augment synergistically the analgesic effect provided by said μ-opiate analgesic, and administration of an effective amount of a NMDA antagonist such as dextromethorphan in an amount effective to augment synergistically the analgesic effect provided by said μ-opiate analgesic. The NMDA antagonist can be administered prior to, concurrently with, or after administration of the μ-opiate analgesic, as long as the dosing interval of NMDA antagonist overlaps with the dosing interval of the μ-opiate analgesic and/or its analgesic effects. The capsaicin or an ester of capsaicin can be administered prior to, concurrently with, or after administration of the μ-opiate analgesic, as long as the dosing interval of the capsaicin or an ester of capsaicin overlaps with the dosing interval of the μ-opiate analgesic and/or its analgesic effects. In other words, according to the method of the present invention, in certain preferred embodiments the NMDA antagonist and the capsaicin or an ester of capsaicin need not be administered in the same dosage form or even by the same route of administration as the µ-opiate analgesic. Rather, the method is directed to the surprising synergistic and/or additive analgesic benefits obtained in humans or other mammals, when analgesically effective levels of an µ-opiate analgesic have been administered to a human or other mammals, and, prior to or during the dosage interval for the µ-opiate analgesic or while the human or other mammal is experiencing analgesia, an effective amount of NMDA antagonist and capsaicin or an ester of capsaicin to augment the analgesic effect of the µ-opiate analgesic is administered. If the NMDA antagonist and the capsaicin or an ester of capsaicin are administered prior to the administration of the µ-opiate analgesic, it is preferred that the dosage intervals for the two drugs overlap, i.e., such that the analgesic effect over at least a portion of the dosage interval of the µ-opiate analgesic is at least partly coincident with the period of useful therapeutic effect of the NMDA antagonist and the capsaicin or an ester of capsaicin.

In an additional method of the invention, the surprising synergistic and/or additive benefits obtained in humans are achieved when analgesically effective levels of a µ-opiate analgesic have been administered to a human during the time period of the therapeutic effect of a NMDA antagonist and capsaicin or an ester of capsaicin. Alternatively the method comprises the effective analgesia obtained when the human or other mammal is experiencing analgesia by virtue of the administration of NMDA antagonist and capsaicin or an ester of capsaicin and an effective amount of a µ-opiate analgesic to synergistically augment the analgesic effect of the µ-opiate analgesic.

In a further embodiment of the present invention, the invention comprises an oral solid dosage form comprising an analgesically effective amount of an µ-opiate analgesic together with an amount of a NMDA antagonist and capsaicin or an ester of capsaicin which augment the effect of the µ-opiate analgesic.

Optionally, the oral solid dosage form includes a sustained release carrier that effectuates the sustained release of the µ-opiate analgesic, or both the µ-opiate analgesic and the NMDA antagonist when the dosage form contacts gastrointestinal fluid. The sustained release dosage form may comprise a multiplicity of substrates and carriers that include the drugs. The substrates may comprise matrix spheroids or may comprise inert pharmaceutically acceptable beads that are coated with the drugs. The coated beads are then preferably overcoated with a sustained release coating comprising the sustained release carrier. The matrix spheroid may include the sustained release carrier in the matrix itself, or the matrix may comprise a simple disintegrating or prompt release matrix containing the drugs, the matrix having a coating applied thereon which comprises the sustained release carrier. In yet other embodiments, the oral solid dosage form comprises a tablet core containing the drugs within a normal or prompt release matrix with the tablet core being coated with a sustained release coating comprising the sustained release carrier.

In yet further embodiments, the tablet contains the drugs within a sustained release matrix comprising the sustained release carrier. In yet further embodiments, the tablet contains the µ-opiate analgesic within a sustained release matrix, and the NMDA antagonist and capsaicin or an ester of capsaicin coated into the tablet as an immediate release layer.

In many preferred embodiments of the invention, the pharmaceutical compositions containing the NMDA antagonist, capsaicin or an ester of capsaicin and µ-opiate drugs set forth herein are administered orally. Such oral dosage forms may contain one or all of the drugs in immediate or sustained release form. For ease of administration, it is preferred that the oral dosage form contains all the three drugs. The oral dosage forms may be in the form of tablets, troches, lozenges, aqueous, solid or semi-solid solutions or mixtures, or oily suspensions or solutions, dispersible powders or granules, emulsions, multiparticulate formulations, syrups, elixirs, and the like.

In other embodiments, a pharmaceutical composition containing the NMDA antagonist, capsaicin or an ester of capsaicin and µ-opiate drugs can be administered in dosage form as a topical preparation, a solid state and or depot type transdermal delivery device(s), a suppository, a buccal tablet, or an inhalation formulation such as a controlled release particle formulation or spray, mist or other topical vehicle, intended to be inhaled or instilled into the sinuses.

The pharmaceutical compositions containing the NMDA antagonist, capsaicin or an ester of capsaicin and/or the µ-opiate drugs set forth herein may alternatively be in the form of microparticles such as microcapsules, microspheres and the like, which may be injected or implanted into a human patient, or other implantable dosage forms known to those skilled in the art of pharmaceutical formulation. For ease of administration, it is preferred that such dosage forms contain each drug.

Similarly, pharmaceutical compositions essentially free of a NSAID or acetaminophen and comprising a combination of a NMDA antagonist and a µ-opiate analgesic can be prepared in solid oral dosage forms or other dosage forms as described above. Accordingly, the pharmaceutical compositions can be administered orally, by means of an implant, parenterally, sub-dermally, sublingually, rectally, topically, or via inhalation.

Another embodiment of the invention is directed to a method of alleviating pain without the use of a narcotic analgesic. The method comprises administering to a patient a pharmaceutical composition comprising a NMDA antagonist, capsaicin or an ester of capsaicin and a µ-opiate analgesic, or comprising a pharmaceutical composition essentially free of a NSAID or acetaminophen and comprising a combination of a NMDA antagonist and a µ-opiate analgesic. In accordance with this embodiment, the active agents can be administered either together or separately, and the patient is not administered a narcotic analgesic.

BRIEF DESCRIPTION OF THE DRAWING

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Definition of Terms

It should be understood that for purposes of the present invention, the following terms have the following meanings:

The term "effective analgesia" is defined for purposes of the present invention as a satisfactory reduction in or elimination of pain, along with the production of a tolerable level of side effects, as determined by the human patient.

The term "effective pain management" is defined for the purposes of the present invention as the objective evaluation or opinion of a human patient's response (pain experienced versus side effects) to analgesic treatment by a physician as well as subjective evaluation of therapeutic treatment by the patient undergoing such treatment. The skilled artisan will understand that effective analgesia will vary widely according to many factors, including individual patient variables.

The term "μ-opiate analgesic" is defined for purposes of the present invention as the drug in its base form, or a pharmaceutically acceptable salt or complex thereof.

The term "dextromethorphan" is defined for purposes of the present invention as the drug in its base form, or a pharmaceutically acceptable salt or complex thereof.

The term "sustained or controlled release" is defined for purposes of the present invention as the release of the drug (μ-opiate analgesic) from the transdermal formulation at such a rate that blood (plasma) concentrations (levels) of the drugs are maintained within the therapeutic range that is above the minimum effective analgesic concentration or "MEAC", but below toxic levels over a period of time of several hours to several days.

The term "steady state" means that the blood plasma time/concentration curve for a given drug level has been substantially stable within a set range from dose to dose.

The term "minimum effective analgesic concentration" or "MEAC" is defined for purposes of this invention as the minimum effective therapeutic blood plasma level of the drug at which at least some pain relief is achieved in a given patient. It will be well understood by those skilled in the medical art that pain measurement is highly subjective and great individual variations may occur among patients.

It must be noted that, as used in this specification, the singular forms "a," "an" and "the" include plural referents unless the context clearly dictates otherwise. Thus, for example, reference to "a pharmacologically active agent" includes a combination of two or more pharmacologically active agents, and the like. In describing the present invention, the following terminology will be used in accordance with the definitions set out below.

As used herein in the claim(s), when used in conjunction with the word "comprising", the words "a" or "an" may mean one or more than one. As used herein "another" may mean at least a second or more.

Figure 1:
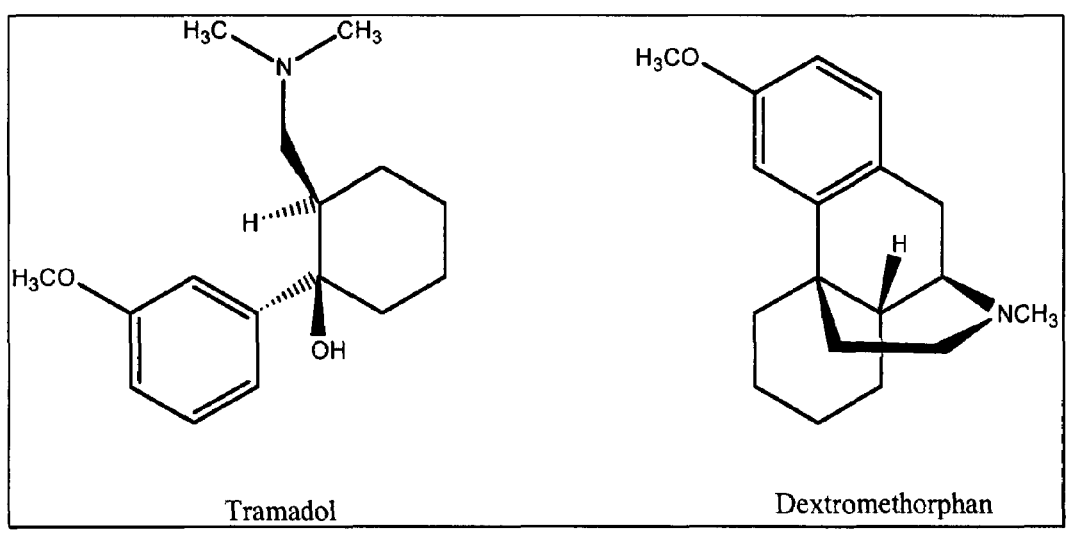
FIG. 1 provides the chemical structures of certain compounds which can be used in practicing the present invention.
Figure 2:
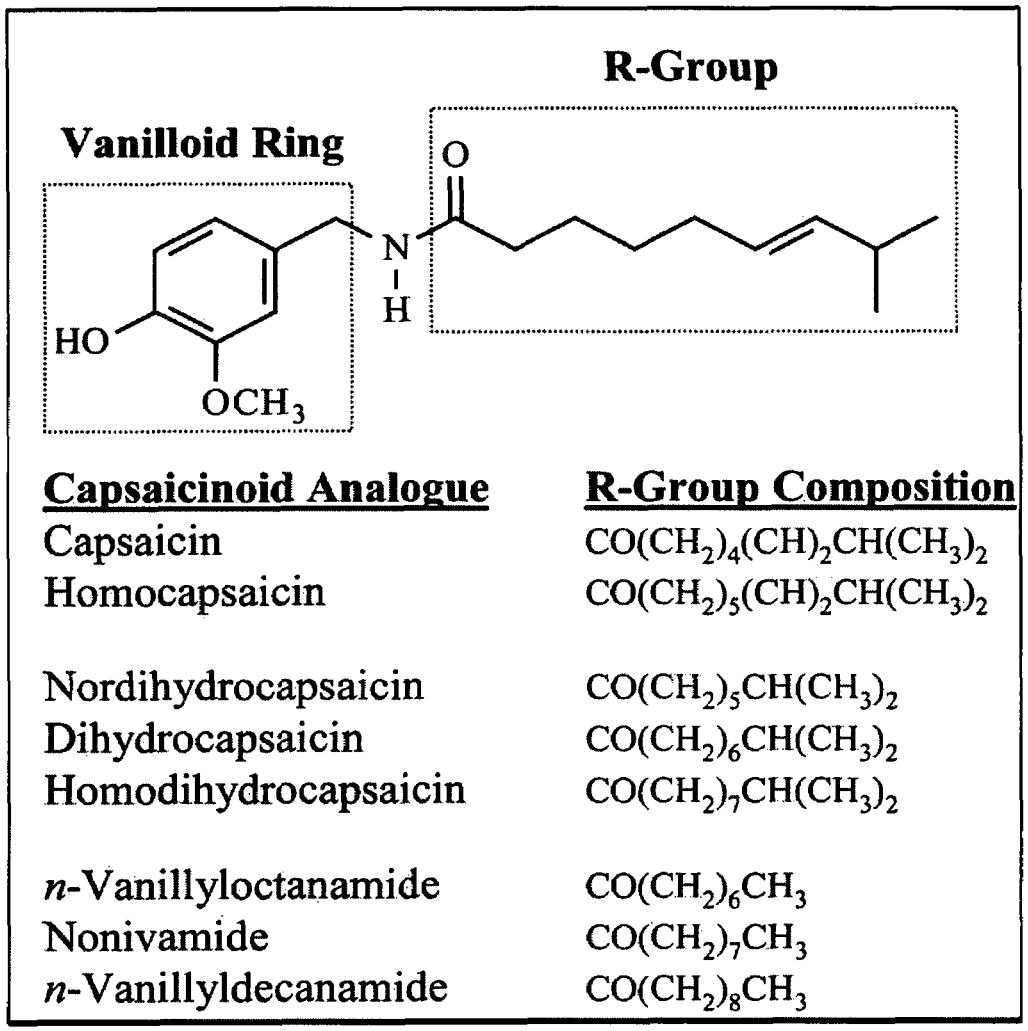
FIG. 2 provides the chemical structures of capsaicin.

The term "capsaicin" or "capsaicins" as used herein is intended to encompass not only the compound capsaicin, but also homocapsaicin, nordihydrocapsaicin, dihydrocapsaicin, homodihydrocapsaicin or any compounded mixture thereof (see FIG. 2).

Figure 3:
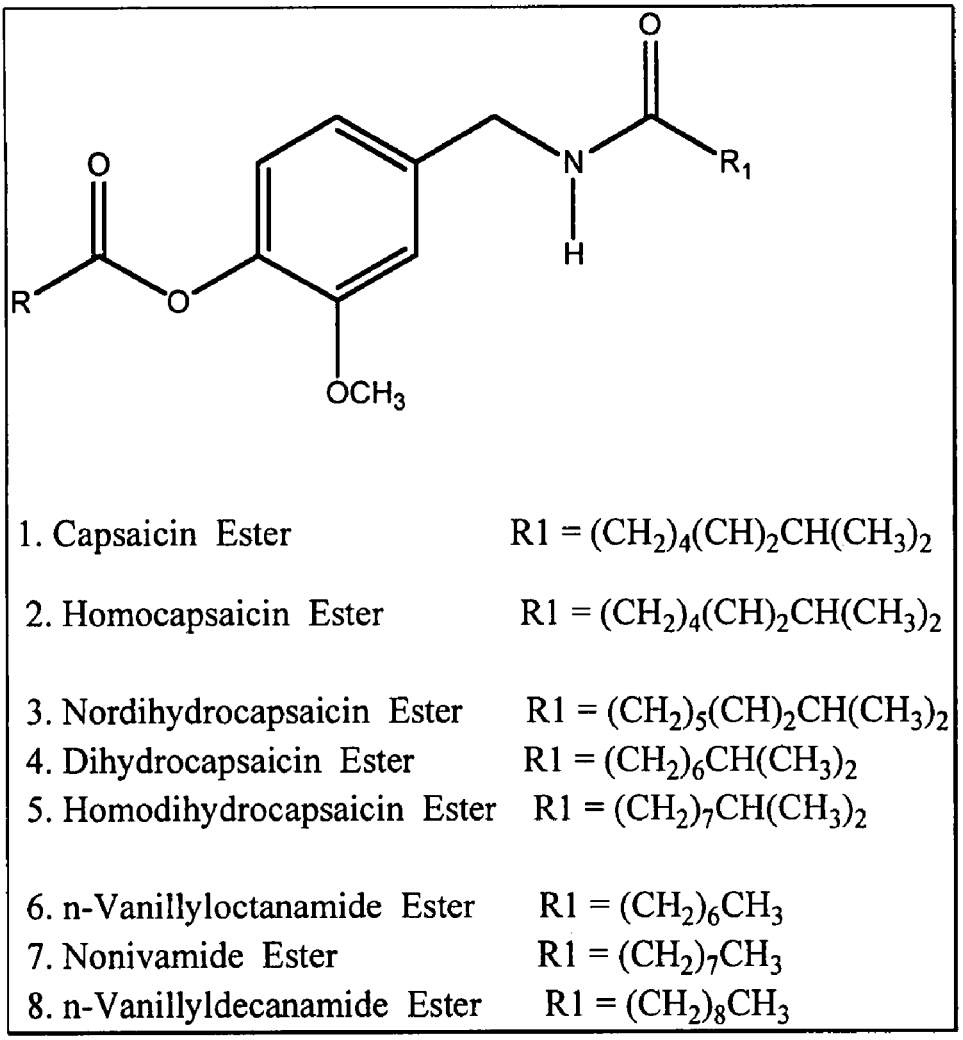
FIG. 3 provides the chemical structures of certain esters of capsaicin.

The term "ester derivatives of capsaicin" or "ester of capsaicin" refers to the acylated derivatives of capsaicin and is denoted by the formula I (see FIG. 3). The pharmaceutical composition and their utilities have been disclosed in a different patent application. These derivatives are capable of reverting to the active parent compound following enzymatic or chemical hydrolysis. These derivatives have a higher lipophilicity, lipid solubility and less irritation to the skin than the parent compound, and hence are better able to be incorporated into certain pharmaceutical formulations, including cream and ointment pharmaceutical formulations. The compounds of the present invention are set forth by the following formula:

$$R\text{---}CO\text{---}CAP \qquad (I)$$

wherein CAP refers to collectively the capsaicins represented in FIG. 2.

In formula I, R is selected from alkyl groups of up to about 22 carbon atoms and aryl groups of up to about 22 carbon atoms and alkylene group of up to about 22 carbon atoms and an arylene group of up to about 22 carbon atoms. The alkyl, aryl and alkylene groups may be substituted or unsubstituted, branched or straight chains. In addition, R may contain heteroatoms and may be straight chained or branched.

Examples of suitable straight-chain alkyl groups in formula I include methyl, ethyl, propyl, butyl, hexyl, heptyl, octyl, dodecyl, 1-pentadecyl, 1-heptadecyl and the like groups.

Examples of suitable branched chain alkyl groups in formula I include isopropyl, sec-butyl, t-butyl, 2-methylbutyl, 2-pentyl, 3-pentyl and the like groups.

Examples of suitable cyclic alkyl groups in formula I include cyclopropyl, cyclobutyl, cyclopentyl and cyclohexyl groups.

Examples of suitable "alkenyl" groups in I include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula I are pyridinyl, thienyl or imidazolyl.

As noted herein, the expression "halo" is meant in the conventional sense to include F, Cl, Br, and I.

Among the compounds represented by the general Formula I, preferred compounds are such in which R is one of the following groups: methyl, ethyl, propyl, butyl, pentyl, hexyl, 1-pentadecyl, 1-heptadecyl, isobutyl, methoxyethyl, ethoxyethyl, benzyl and nicotinyl. The compounds of Formula I are esters of capsaicin present in capsicum.

Description of the Applications of the Invention

The pharmacological management of acute postoperative pain and chronic pain syndromes has been traditionally based on various regimens of opiates and their congeners or NSAIDs. All opiates have side effects, of which the most dangerous are respiratory and cardiovascular depression associated with excessive sedation. NSAIDs may also induce side effects such as exacerbation of bleeding tendencies and the impairment renal function. The search for alternative pain control strategies has focused on the N-methyl-D-aspartate (NMDA) receptors and their antagonists which were recently shown to alleviate somatic and neuropathic pain sensation in both animal and human models (Plesan et al, 1998, Klepstad et al, 1990, Eisenberg et al, 1998, Kinnman et al, 1997 and Kawamatugs to a et al, 1998). The clinical utility of these agents stems from the high affinity binding of the drugs to NMDA receptors resulting in blockade of the NMDA receptors located at the junction where pain is generated by peripheral nociceptive stimuli and is thence conveyed to central receptors via A* and C sensory fibres (Woolf et al, 1993). From a clinical standpoint, the amounts of conventional pain killers that are needed for effective pain. control would be much smaller. One of these compounds is dextromethorphan (DM), a low affinity, non-competitive NMDA receptor antagonist that has a long history of clinical safety as a cough suppressant (Bem et. al, 1992).

Considerable evidence has accumulated over the past few years on the role of excitatory amino acids (EAA), such as glutamate and aspartate, in modulating the sensation of pain via the ascending pathways along the spinal cord and central nervous system. The stimulation of NMDA receptors located in the dorsal horn of the spinal cord, the area responsible for relaying, modulating and transmitting pain, by intraspinal deposition of glutamate in experimental rat and monkey models generated an increased response to noxious stimuli and lowered the threshold of pain (Battaglia et al, 1988; Aanonsen et. al. 1987). This response was successfully abolished by administration of NMDA antagonists, such as phencyclidine, suggesting that the pain can be attenuated by blocking the activity of these receptors.

Investigations of chronic pain syndromes revealed that the same mechanisms are involved in the initiation and the perpetuation of secondary pain in mouse and rat models. In terms of neurophysiology, following acute tissue injury, transduction is accomplished by action potentials being generated at the nerve endings and transmitted along the A* and C fibres to the synapses of the dorsal part of the spinal cord where they induce the release of various peptides, including EAA. The EAA activate the NMDA receptors that are located within the synapses, thus stimulating the synaptic neurons to transmit sensations of pain. This state of hyperexcitability, or "wind up" amplifies the magnitude and duration of neurogenic responses to any existing volley of nociceptive activity. Once initiated, this state of hyperex-citability can exist even after the peripheral input has ceased Dickenson 1995). This phenomenon is currently thought to be responsible for various clinical pain syndromes such as allodynia, an intense sensation of pain following a relatively minor stimulus that would not ordinarily induce pain sensation or hyperpathia, a sensation of pain that persists long after the initial nociceptive stimulus has subsided (Davies et al, 1987; Felsby et al, 1995).

The role of NMDA in the "wind up" phenomenon of pain perception was clarified in animals by intraspinal administration of NMDA-receptor antag-onists (Dickenson 1990; Dickenson et al, 1990). In one human study, i.v. ketamine reduced the magnitude of both primary (immediate) and sec-ondary hyperalgesia and the pain evoked by prolonged heat stimulation in a dose-dependent manner (Ilkjaer et al, 1996). DM acts in a similar manner: Klepstad et al, published a case report of a patient who had undergone four years of satisfactory ketamine treatment for postherpetic neuralgia. Experimental substitution of the ketamine by DM 125 mg in four divided doses for seven days was found to be as efficient. Here it is important to note that the NMDA receptors are widespread throughout the central nervous system, and as such, are associated with highly diverse neurophysiological functions as far removed from the modulation of pain as learning and memory processing.

It is therefore not surprising that their antagonists can interfere with its physiological activity, leading to sedation, motor dysfunction or altered behavior. Antagonism of the potentially deleterious effects of an excessive release of EAA, such as that which occurs in patients with focal brain ischemia (an example of the diversity of NMDA activity) can lead to episodes of agitation, hallucinations, somnolence, nausea, vomiting and nystagmus (Grotta et al, 1995, Albers et al, 1995, Muir et al, 1995). This is why so few NMDA receptor antagonists have been tested in humans despite their effectiveness in pain management, and despite the extensive animal data that point to their promising beneficial effect (Roytblat et al, 1993, Mercadante et al, 1996, Kornhuber et al, 1995).

To date DM, ketamine and amantadine are the only drugs with NMDA receptor antagonistic properties that are FDA approved drugs for clinical use. However, due to the high affinity of ketamine to its receptors and its related dysphoric effects, together with the need to administer it intravenously, research in pain control has turned its focus to DM as the preferred NMDA antagonist for clinical use.

Dextromethorphan and levorphanol were originally synthesized as pharmacological alternatives to morphine more than 40 years ago. DM is the D isomer of the codeine analogue, levorphanol but, in contrast to its L isomer, it has no effect on the opiate receptors (Benson et al, 1953). From the beginning, its clinical use was mainly that of an antitussive in syrup preparations, at adult doses of 10 to 30 mg three to six times daily. The specific central sites upon which DM exerts its antitussive effect are still uncertain, but they are distinct from those of opiates, insofar as the effect is not suppressed by naloxone (Karlsson et al, 1988). Also, unlike opiates, DM has an established safety record, i.e., the therapeutic cough suppressant dose (1 $mg \cdot kg^{-1} \cdot dy^{-1}$) has no major opiate like respiratory or hemodynamic side effects, neither does it induce histamine release complications. The binding of the antagonists to the NMDA receptors results in modifying the receptor-gated $Ca^{2+}$ current. Changes in the $Ca^{2+}$ current normally lead to NMDA induced neuronal firing which, if it persists, is followed by a heightening of the intensity of the primary nociceptive stimulus, i.e., "wind up" phenomenon, and the triggering of secondary sensory pain (Mendell 1966; Church et al, 1985). In contrast to the other NMDA receptor antagonists, DM has widespread binding sites in the central nervous system that are distinct from those of opiates and other neurotransmitters, so that its activity is not limited to the NMDA receptors alone, as was shown in pigs and rats (Musacchio 1988, Church 1991). Besides the ability of DM to reduce intracellular $Ca^{2+}$ influx through the NMDA receptor-gated channels, DM also regulates voltage-gated $Ca^{2+}$ channels that are normally activated by high concentrations of extracellular $K^+$. One of the physiological consequences of these multi-channel regulation capabilities is the attenuation by DM of NMDA mediated neuronal firing in the brain that is normally transformed into seizures, as was shown experimentally in rats and in neuronal cell cultures as well as in humans (Ferkany 1988, Choi 1987).

The neuropharmacological cascade of events that provokes the reduced intracellular accumulation of $Ca^{2+}$ to cause changes in the activity of NMDA receptors remains to be elucidated. In humans as in animals, DM was also capable of ameliorating discomfort associated with excitotoxicity-related neurological disorders, such as intractable seizures and Parkinson's disease when administered at doses of 30 or 60 mg q. i.d. (Albers 1991), 45 to 180 mg p.o. (Bonuccelli et al, 1991) or 120 mg p.o. (Fisher et al, 1990) for periods of three weeks to three months. No serious untoward neurological effects were detected in these and in another study where eight healthy human volunteers in whom motor cortex excitability, as indicated by motor-evoked potentials, was reduced after a single oral high (150 mg) dose (Ziemann et al, 1998). In addition, motor cortex excitability and levodopa-induced dyskinesis were reduced by DM at a dose of 100 mg in a double-blind placebo-control study in patients with Parkinson's disease, (Verhagen et al, 1998) with only negligible side effects.

Elaboration of the Properties of the Preferred Active Ingredients

Dextromethorphan is rapidly metabolized in the liver (Woodworth et al, 1987) where it is transformed to dextrorphan, its active and more potent derivative as a NMDA antagonist. It was suggested that the side effects documented in clinical studies and attributed to the oral administration of DM might be mediated by this metabolite acting at the phencyclidine receptorial site rather than DM itself (Musacchio et al, 1989).

Satisfactory pain control achieved with the least amount of opiates has always been an important goal in view of both the psychological and somatic dependence these drugs may induce and the often intolerable side effects that may follow their extensive use. The searchers for techniques of pain control that will afford full orientation, coordination and collaboration, and normal respiration as well as stable hemodynamics view these factors as important cornerstones in postoperative planning of pain control. This applies equally to patients who had undergone either general or regional anesthesia and to inpatients as well as outpatients. Moreover, in view of the contention that persistent NMDA receptor activation can evoke central hyperexcitability that can lead to secondary pain, proper pain control should both modulate primary pain sensation and preempt an analgesic state that would prevent acute pain from progressing into chronic pain. This concept of preemptive analgesia (i.e., reducing pain sensation in advance) is feasible via NMDA modulation, as had been demonstrated by the administration of opiates and ketamine to patients before surgery (Kiss et al, 1992, Tverskoy et al, 1994). Importantly, this neuropharmacological receptor conditioning is also beneficial for reducing the need for additional doses of opiates post-operatively. In addition, while the neurovegetative stimulation and adrenergic overproduction that accompany the continuous neurally transmitted acute and, to a greater extent, secondary pain are clearly detrimental to all patients, they may be particularly harmful for cardiac patients. In this regard, the preemptive approach is an especially promising and beneficial one. The use of DM may, therefore, become an established component in protocols of treating pain and of alleviating the accompanying neurovegetative phenomena. Finally, the bioavailability of DM administered orally makes it much more convenient than the other anti-NMDA drugs, all of which are administered by injection, such as ketamine. As a potential morphine sparing agent for pain, the use of DM was shown to be efficient and well tolerated (Henderson et al, 1999).

It is noteworthy that NMDA receptor antagonists, including DM, are not in themselves anti-nociceptive (Ilkjaer 1997) but rather they inhibit central sensitization and, thus, the perception of primary and secondary pain (Price et al, 1994; Chia et al, 1999). The preemptive use of these antagonists, while blunting the development of a central sensitization of a nociceptive stimulus (Yamamoto et al, 1992), still requires the use of an analgesic for complete abolition of pain perception.

(+/-)-Tramadol is a synthetic 4-phenyl-piperidine analogue of codeine. It is a central analgesic with a low affinity for opiate receptors. Its selectivity for mu receptors has recently been demonstrated, and the M1 metabolite of tramadol, produced by liver O-demethylation, shows a higher affinity for opiate receptors than the parent drug. The rate of production of this M1 derivative (O-demethyl tramadol), is influenced by a polymorphic isoenzyme of the debrisoquine-type, cytochrome P450 2D6 (CYP2D6). One mechanism relates to its weak affinity for μ-opiate receptors (6,000-fold less than morphine, 100-fold less than d-propoxyphene, 10-fold less than codeine, and equivalent to dextromethorphan). Moreover, and in contrast to other opiates, the analgesic action of tramadol is only partially inhibited by the opiate antagonist naloxone, which suggests the existence of another mechanism of action. This was demonstrated by the discovery of a monoaminergic activity that inhibits noradrenaline (norepinephrine) and serotonin (5-hydroxytryptamine; 5-HT) reuptake, making a significant contribution to the analgesic action by blocking nociceptive impulses at the spinal level (Dayer et al, 1994 & 1997).

(+/-)-Tramadol is a racemic mixture of 2 enantiomers, each one displaying differing affinities for various receptors. (+/-)-tramadol is a selective agonist of μ receptors and preferentially inhibits serotonin reuptake, whereas (-)-tramadol mainly inhibits noradrenaline reuptake. The action of these 2 enantiomers is both complementary and synergistic and results in the analgesic effect of (+/-)-tramadol. After oral administration, tramadol demonstrates 68% bioavailability, with peak serum concentrations reached within 2 hours. The elimination kinetics can be described as 2-compartmental, with a half-life of 5.1 hours for tramadol and 9 hours for the M1 derivative after a single oral dose of 100 mg. This explains the approximately 2-fold accumulation of the parent drug and its M1 derivative that is observed during multiple dose treatment with tramadol. The recommended daily dose of tramadol is between 50 and 100 mg every 4 to 6 hours, with a maximum dose of 400 mg/day. The duration of the analgesic effect after a single oral dose of tramadol 100 mg is about 6 hours. Adverse effects, and nausea in particular, are dose dependent and therefore considerably more likely to appear if the loading dose is high. The reduction of this dose during the first days of treatment is an important factor in improving tolerability. Other adverse effects are generally similar to those of opiates, although they are usually less severe, and can include respiratory depression, dysphoria and constipation. Tramadol can be administered concomitantly with other analgesics, particularly those with peripheral action, while drugs that depress CNS function may enhance the sedative effect of tramadol. Tramadol has pharmacodynamic and pharmacokinetic properties that are highly unlikely to lead to dependence. This was confirmed by various controlled studies and postmarketing surveillance studies, which reported an extremely small number of patients developing tolerance or instances of tramadol abuse (Raffa et al, 1993; Lee et al, 1993). Although it has proven to be a safe and effective agent for the control of pain, adverse effects can occur with its use. It has been reported the occurrence of seizure activity after the inadvertent administration of 4 mg/kg of tramadol to a child (Tobias 1997).

Capsaicin is a natural constituent in pungent red chili peppers. Depending on the concentration used and the mode of application, capsaicin can selectively activate, desensitize, or exert a neurotoxic effect on small diameter sensory afferent nerves while leaving larger diameter afferents unaffected (Holzer, 1991; Winter et al, 1995). Sensory neuron activation occurs due to interaction with a ligand-gated nonselective cation channel termed the vanilloid receptor (VR-1) (Caterina et al, 1997), and receptor occupancy triggers $Na^+$ and $Ca^{2+}$ ion influx, action potential firing, and the consequent burning sensation associated with spicy food or capsaicin-induced pain. VR1 receptors are present on both C and Aδ fibers, and can be activated by capsaicin and its analogs, heat, acidification, and lipid metabolites (Tominaga et al, 1998; Caterina and Julius, 2001). Desensitization occurs with repeated administration of capsaicin, is a receptor-mediated process, and involves $Ca^{2+}$- and calmodulin-dependent processes and phosphorylation of the cation channel (Winter et al, 1995; Wood and Docherty, 1997).

Capsaicin induces release of substance P and calcitonin gene-related peptide from both peripheral and central terminals of sensory neurons, and desensitization inhibits such release (Holzer, 1991); such inhibition may result from inhibition of voltage-gated $Ca^{2+}$-currents (Docherty et al, 1991; Winter et al, 1995). Desensitization leads to analgesia in rodent paradigms, with specific characteristics of analgesia depending on the dose of capsaicin, route of administration, treatment paradigm (i.e., acute or repeated administration), and age of the animal (Holzer, 1991; Winter et al, 1995). The topical skin application of capsaicin to rodents produces analgesia (Kenins, 1982; Lynn et al, 1992), but variability in outcome can occur due to the concentration, the number of applications, and the different vehicles used that can affect the rate and extent of skin penetration (Carter and Francis, 1991; McMahon et al, 1991).

Viral replication, immune regulation, and induction of various inflammatory and growth-regulatory genes require activation of a nuclear transcription factor (NF)-κ-B. Agents that can block NF-κ-B activation have potential to block downstream responses mediated through this transcription factor. Capsaicin (8-methyl-N-vanillyl-6-nonenamide) has been shown to regulate a wide variety of activities that require NF-κ-B activation (Singh 1996). The pretreatment of human myeloid ML-1a cells with capsaicin blocked TNF-mediated activation of NF-κ-B in a dose- and time-dependent manner. Capsaicin treatment of cells also blocked the degradation of I-κ-B alpha, and thus the nuclear translocation of the p65 subunit of NF-κ-B, which is essential for NF-κ-B activation. TNF-dependent promoter activity of I-κ-B alpha, which contains NF-κ-B binding sites, was also inhibited by capsaicin.

Acute intradermal injection of capsaicin to the skin in humans produces a burning sensation and flare response; the area of application becomes insensitive to mechanical and thermal stimulation, the area of flare exhibits a primary hyperalgesia to mechanical and thermal stimuli, and an area beyond the flare exhibits secondary allodynia (Simone et al, 1989; LaMotte et al, 1991). Repeated application to normal skin produces desensitization to this response and thus forms the basis of the therapeutic use of topical capsaicin in humans. Desensitization involves both physiological changes in the terminals of the sensory neuron noted above, as well as a degree of loss of sensory fiber terminals within the epidermis (Nolano et al, 1999).

Topical capsaicin preparations of 0.025 and 0.075% are available for human use, and these produce analgesia in randomized double-blind placebo-controlled studies, open label trials, and clinical reports (Watson, 1994; Rains and Bryson, 1995). Topical capsaicin produces benefit in postherpetic neuralgia (Bernstein et al, 1989; Watson et al, 1993), diabetic neuropathy (Capsaicin Study Group, 1992), postmastectomy pain syndrome (Watson and Evans, 1992; Dini et al, 1993), oral neuropathic pain, trigeminal neuralgia, and temperomandibular joint disorders (Epstein and Marcoe, 1994; Hersh et al, 1994), cluster headache (following intranasal application) (Marks et al, 1993), osteoarthritis (McCarthy and McCarthy, 1992), and dermatological and cutaneous conditions (Hautkappe et al, 1998). Whereas pain relief is widely observed in these studies, the degree of relief is usually modest, although some patients have a very good result. Topical capsaicin is generally not considered a satisfactory sole therapy for chronic pain conditions and is often considered an adjuvant to other approaches (Watson, 1994). No significant benefit was reported in chronic distal painful neuropathy (Low et al, 1995) or with human immunodeficiency virus-neuropathy (Paice et al, 2000).

The distribution and metabolism of capsaicin and/or dihydrocapsaicin has been studied in rats. Capsaicin is distributed to the brain, spinal cord, liver and blood within 20 mins. of i.v. administration. Oral doses of dihydrocapsaicin in the rat showed metabolic activity associated with its absorption into the portal vein. Capsaicin and dihydrocapsaicin are metabolized in the liver by the mixed-function oxidation system (cytochrome P-450-dependent system). It is assumed that capsaicin is excreted in urine. In rats, most of dihydrocapsaicin is known to be rapidly metabolized and excreted in the urine (Rumsfield and West, 1991).

Oral dosing of rats with capsaicin and dihydrocapsaicin results in an 85% absorption in the jejunum after 3 hours (Rumsfield and West, 1991). With respect to topical applications of capsaicin, it has been estimated that assuming 100% of a topically-applied dose is absorbed into the body, an application of 90 g capsaicin (2 tubes of cream, 0.025% capsaicin) per week would result in a daily exposure of 0.064 mg/kg capsaicin for a 50 kg person. This represents less than 10% of the dietary intake of a typical Indian or Thai diet (Rumsfield and West, 1991).

The most frequently encountered adverse effect with capsaicin is burning pain at the site of application, particularly in the first week of application. This can make it impossible to blind trials and can lead to dropout rates ranging from 33 to 67% (Watson et al, 1993; Paice et al, 2000). Another factor in compliance is the time delay before therapeutic effect is observed (at least a week, but sometimes several weeks). One approach toward minimizing adverse effects and accelerating the rate of analgesia has been to deliver a higher capsaicin concentration (5-10%) under regional anesthesia, and this produced sustained analgesia lasting 1 to 8 weeks in cases of complex regional pain syndrome and neuropathic pain (Robbins et al, 1998). When topical local anesthetics were applied with 1% topical capsaicin, no alteration in pain produced by the capsaicin was observed in healthy subjects (Fuchs et al, 1999) indicating that this cotreatment was not sufficient to block the pain induced by capsaicin.

Capsaicin is believed to cause depolarization of C-fiber polymodal nociceptors (Lynn 1990; Marsh 1987) and release of substance P, which is a neurotransmitter that relays pain signals to the brain. This action may actually increase pain sensation after initial use. However, repeat applications deplete the reserves of substance P at the afferent neurons leading to pain relief (Nolano 1999). Depletion of substance P does not occur immediately. Effective use of the cream (0.075% capsaicin) requires topical application 4 or 5 times daily for a period of at least 4 weeks.

In order to make the capsaicins to have less irritation to the skin and significantly less burning sensation to the stomach, the capsaicins have been esterified at the phenolic position. These esters have the general formula I,

R—CO-CAP        (I)

wherein CAP refers to collectively the capsaicins represented in FIG. 2.

In formula I, R is selected from alkyl groups of up to about 18 carbon atoms and aryl groups of up to about 18 carbon atoms and alkylene group of up to about 18 carbon atoms and an arylene group of up to about 18 carbon atoms. The alkyl, aryl and alkylene groups may be substituted or unsubstituted, branched or straight chains. In addition, R may contain heteroatoms and may be straight chained or branched.

Examples of suitable straight-chain alkyl groups in formula I include methyl, ethyl, propyl, butyl, hexyl, heptyl, octyl, dodecyl, 1-pentadecyl, 1-heptadecyl and the like groups.

Examples of suitable branched chain alkyl groups in formula I include isopropyl, sec-butyl, t-butyl, 2-methylbutyl, 2-pentyl, 3-pentyl and the like groups.

Examples of suitable cyclic alkyl groups in formula I include cyclopropyl, cyclobutyl, cyclopentyl and cyclohexyl groups.

Examples of suitable "alkenyl" groups in I include vinyl (ethenyl), 1-propenyl, i-butenyl, pentenyl, hexenyl, n-decenyl and c-pentenyl and the like.

The groups may be substituted, generally with 1 or 2 substituents, wherein the substituents are independently selected from halo, hydroxy, alkoxy, amino, mono- and dialkylamino, nitro, carboxyl, alkoxycarbonyl, and cyano groups.

By the expression "phenalkyl groups wherein the alkyl moiety contains 1 to 3 or more carbon atoms" is meant benzyl, phenethyl and phenylpropyl groups wherein the phenyl moiety may be substituted. When substituted, the phenyl moiety of the phenalkyl group may contain independently from 1 to 3 or more alkyl, hydroxy, alkoxy, halo, amino, mono- and dialkylamino, nitro, carboxyl, alkoxycarbonyl and cyano groups.

Examples of suitable "heteroaryl" in formula I are pyridinyl, thienyl or imidazolyl.

As noted herein, the expression "halo" is meant in the conventional sense to include F, Cl, Br, and I.

Among the compounds represented by the general Formula I, preferred compounds are such in which R is one of the following groups: methyl, ethyl, propyl, butyl, pentyl, hexyl, 1-pentadecyl, 1-heptadecyl, isobutyl, methoxyethyl, ethoxyethyl, benzyl and nicotinyl.

The compounds esters of capsaicin can be prepared by any method known to those of ordinary skill in the art. For example, the compounds of the present invention are esters of capsaicin which are the constituents of capsicum. Various methods have been described in the literature pertaining to the synthesis of a number of esters of carboxylic acids and phenols (March's Advanced Organic Chemistry: Reactions, Mechanisms, and Structure, 5th Edition, by Michael B. Smith and Jerry March, John Wiley and Sons, Inc, 2001).

One method that has been utilized for efficient preparation of the ester of capsaicin used in the present invention is through dissolution of the compound in methylene dichloride. Since capsaicin USP27 contains >95% of capsaicins, to this solution slightly in excess of 1.1 mole equivalent of anhydrous triethylamine is added with stirring at room temperature. To this solution slightly in excess of 1 mole equivalent of an acid chloride is added with stirring while keeping the temperature at room temperature. After that, the solution was refluxed for 6-8 hours and stirred for 18-24 hours at room temperature. The organic phase was washed 3-4 times with dilute hydrochloric acid solution in a separating funnel to remove any amine present in the organic solution. The reaction mixture was then washed with equal amount of water three to four times to remove the unreacted amine and its salt in a separating funnel. The organic phase was dried with anhydrous sodium sulfate overnight and the methylene dichloride was removed in a rotary evaporator under vacuum. The resultant oily or waxy material is called the ester capsaicin as all of the phenols present capsaicin is converted into the corresponding ester.

For oral administration, the preferred ester is the palmitate esters of capsaicins. These esters have less irritation and burning sensation to the stomach and are used for relieving pain through its binding to the VR1 receptors and the depletion of substance P.

Description of Alternative Ingredients

A non-limiting list of μ-opiate analgesic drugs which may be utilized in the present invention include any one of (1R,2R or 1S,2S)-(dimethylaminomethyl)-1-(3-methoxyphenyl)-cyclohexanol (tramadol), its N-oxide derivative ("tramadol N-oxide"), and its O-desmethyl derivative ("O-desmethyl tramadol") or mixtures, stereoisomers, racemates metabolites, salts or complexes thereof.

A non-limiting list of NMDA antagonist drugs which may be utilized in the present invention include dextromethorphan, dextrorphan, ketamine, amantadine, memantine, eliprodil, ifenprodil, phencyclidine, MK-801, dizocilpine, CCPene, flupirtine, or derivatives, salts, metabolites or complexes thereof.

A non-limiting list of capsaicins which may be used in the present invention include capsaicin, homocapsaicin, nordihydrocapsaicin, dihydrocapsaicin, homodihydrocapsaicin, n-vanillyloctanamide, nonivamide and n-vanillyldecanamide or ester derivatives thereof.

Description of Quantitative Pharmacological Parameters of the Mixture

Preferred embodiments of the present invention are analgesic preparations for oral administration that provide a combination of a NMDA antagonist or a pharmaceutically acceptable salt thereof, capsaicin or an ester of capsaicin or an analog thereof, and a μ-opiate analgesic or a pharmaceutically acceptable salt thereof. The combination preferably provides a synergistic or at least additive effect for analgesic dosages.

Dosage levels of the NMDA antagonist on the order of from about 0.1 mg to about 10 mg per kilogram of body weight per day and capsaicin or an ester of capsaicin or its analog on the order of from about 0.02 mg to about 5 mg per kilogram of body weight are therapeutically effective in combination with a μ-opiate analgesic. Alternatively, about 1 mg to about 400 mg per patient per day of a NMDA antagonist and about 1 mg to about 100 mg per patient per day of capsaicin or an ester of capsaicin or its analog are administered in combination with a μ-opiate analgesic. For example, chronic pain may be effectively treated by the administration of from about 0.1 to 10 mg of the NMDA antagonist per kilogram of body weight per day, or alternatively about 10 mg to about 300 mg per patient per day.

The amount of NMDA antagonist that may be combined with the carrier materials to produce a single dosage form having NMDA antagonist, capsaicin or an analog of capsaicin and μ-opiate analgesic in combination will vary depending upon the patient and the particular mode of administration. For example, a formulation intended for the oral administration of humans may contain from 10 mg to 300 mg of NMDA antagonist compounded with an appropriate and convenient amount of carrier material that may vary from about 5 to about 95 percent of the total composition. Unit dosages will generally contain between from about 10 mg to about 100 mg of a NMDA antagonist.

In one embodiment, the μ-opiate analgesic is provided in a sustained release oral dosage form with as the therapeutically active μ-opiate in an amount from about 25 mg to about 400 mg tramadol hydrochloride. Alternatively, the dosage form may contain molar equivalent amounts of other tramadol salts or of the tramadol base. The dosage form may contain more than one µ-opiate analgesic to provide a substantially equivalent therapeutic effect.

Preferred combinations of the invention comprise an effective amount of a NMDA antagonist selected from the group consisting of dextromethorphan, ketamine and amantidine, an effective amount of an µ-opiate analgesic selected from the group consisting of tramadol, its metabolites and analogs and an effective amount of capsaicin or an ester of capsaicin, its analogs.

In certain preferred embodiments according to the present invention, an oral dosage form is preferred which includes the following µ-opiate/NMDA-antagonist/capsaicin or ester of capsaicin combinations: Tramadol 50 mg plus 50 mg dextromethorphan plus 5.6 mg palmitate ester of capsaicin, tramadol 50 mg plus 45 mg dextromethorphan plus 11.2 mg palmitate ester of capsaicin, tramadol 35 mg plus 45 mg dextromethorphan plus 11.2 mg palmitate ester of capsaicin or 50 mg of tramadol plus 30 mg of dextromethorphan plus 11.2 mg palmitate ester of capsaicin.

The amount of capsaicin or an ester of capsaicin in the composition will be an amount sufficient to further enhance analgesia or to hasten its onset. In humans, this amount will typically be from about 1 to about 100 mg (preferably 2.5 to 20 mg), an amount generally sufficient to both hasten onset and enhance analgesia. The daily dosage of capsaicin or an ester of capsaicin again will generally not exceed 50 mg. Of course, greater amounts can be used if tolerated by the patient.

The dosage administered will of course vary depending upon known factors such as the pharmacodynamic characteristics of each agent of the combination and its mode and route of administration and upon the age, health and weight of the patient. The dosage will also depend upon the nature and extent of symptoms, concurrent treatment, if any, frequency of treatment and the desired result. A composition comprising any of the above identified combinations of a µ-opiate analgesics and NMDA antagonist may be administered in divided doses ranging from 2 to 6 times per day or in a sustained release form that will provide a rate of release effective to attain the desired results.

The optimal NMDA antagonist to µ-opiate analgesic ratios are determined by standard assays well known in the art for determining opiate and analgesic activity. For example, the phenyl-p-benzoquinone test may be used to establish analgesic effectiveness. The phenyl-p-benzoquinone induced writhing test in mice as described in H. Blumberg et al, 1965, Proc. Soc. Exp. Med. 118:763-766, hereby incorporated by reference, and known modifications thereof, is a standard procedure which may be used for detecting and comparing the analgesic activity of different classes of analgesic drugs with a good correlation with human analgesic activity. Data for the mouse, as presented in an isobologram, can be translated to other species where the orally effective analgesic dose of the individual compounds are known or can be estimated. The method consists of reading the percent ED50 dose for each dose ratio on the best fit regression analysis curve from the mouse isobologram, multiplying each component by its effective species dose, and then forming the ratio of the amount of NMDA antagonist and µ-opiate analgesic. This basic correlation for analgesic properties enables estimation of the range of human effectiveness as in E. W. Pelikan, 1959, The Pharmacologist 1:73, herein incorporated by reference.

Elaboration of Preferred and Alternative Formulations and Vehicles

The present invention encompasses immediate release dosage forms of an effective analgesic amount of dextromethorphan and µ-opiate analgesic combination. An immediate release dosage form may be formulated as a tablet or multiparticulate that may be encapsulated. Other immediate release dosage forms known in the art can be employed.

Compositions of the invention present the opportunity for obtaining relief from moderate to severe pain. Due to the synergistic and/or additive effects provided by the inventive combination of µ-opiate analgesic, capsaicin or an ester of capsaicin and NMDA antagonist, it may be possible to use reduced dosages of each of NMDA antagonist and opiate analgesic. By using lesser amounts of other or both drugs, the side effects associated with each may be reduced in number and degree. Moreover, the inventive combination avoids side effects to which some patients are particularly sensitive.

The present invention encompasses a method of inhibiting NMDA receptor and treating diseases comprising administering to a patient in need of such treatment a non-toxic therapeutically effective amount of the NMDA antagonist, capsaicin or an ester of capsaicin and µ-opiate analgesic combination of the present invention. These diseases include moderate to severe pain arising from many different etiologies, including but not limited to cancer pain and post-surgical pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases such as osteoarthritis, gout and ankylosing spondylitis, bursitis, burns, symptoms associated with diabetic neuropathy and injuries. Further, the combination of NMDA antagonist, capsaicin or an ester of capsaicin and µ-opiate analgesic is useful as an alternative to conventional non-steroidal anti-inflammatory drugs or combinations of NSAIDS with other drugs particularly where such non-steroidal anti-inflammatory drugs may be contraindicated such as in patients with peptic ulcers, gastritis, regional enteritis, ulcerative colitis, diverticulitis or with a recurrent history of gastrointestinal lesions, GI bleeding, coagulation disorders including anemia such as hypoprothrombinemia, haemophilia or other bleeding problems, kidney disease and in those prior to surgery or taking anticoagulants.

The sustained release dosage forms of the present invention generally achieve and maintain therapeutic levels substantially without significant increases in the intensity and/or degree of concurrent side effects, such as nausea, vomiting, seizures or drowsiness, which are often associated with high blood levels of µ-opiate analgesics. There is also evidence to suggest that the use of the present dosage forms leads to a reduced risk of drug addiction.

The combination of NMDA antagonist capsaicin or an ester of capsaicin and oral µ-opiate analgesics may be formulated to provide for an increased duration of analgesic action allowing once daily dosing. These formulations, at comparable daily dosages of conventional immediate release drug, are associated with a lower incidence in severity of adverse drug reactions and can also be administered at a lower daily dose than conventional oral medication while maintaining pain control.

The combination of NMDA antagonist, capsaicin or an ester of capsaicin and an µ-opiate analgesic can be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For parenteral application, particularly suitable are oily or aqueous solutions, as well as suspensions, emulsions, or implants, including suppositories. For oral application, particularly suitable are tablets, troches, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose, granulating and disintegrating agents such as cornstarch, binding agents such as starch, and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent.

Aqueous suspensions that contain the aforementioned combinations of drugs and that such a mixture has one or more excipients suitable as suspending agents, for example pharmaceutically acceptable synthetic gums such as hydroxypropylmethylcellulose or natural gums. Oily suspensions may be formulated by suspending the aforementioned combinations of drugs in a vegetable oil or mineral oil. The oily suspensions may contain a thickening agent such as bees' wax or cetyl alcohol. A syrup, elixir, or the like can be used wherein a sweetened vehicle is employed. Injectable suspensions may also be prepared, in which case appropriate liquid carriers, suspending agents and the like may be employed. It is also possible to freeze-dry the active compounds and use the obtained lyophilized compounds, for example, for the preparation of products for injection.

The method of treatment and pharmaceutical formulations of the present invention may further include one or more drugs in addition to a NMDA antagonist, capsaicin or an ester of capsaicin and a μ-opiate analgesic, which additional drug(s) may or may not act synergistically therewith. Examples of such additional drugs include NSAIDs, including ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, acetaminophen and the like. Other suitable additional drugs that may be included in the dosage forms of the present invention include acetaminophen, aspirin, and other non-opiate analgesics.

Controlled Release Dosage Forms

The NMDA antagonist, capsaicin or an ester of capsaicin and μ-opiate analgesic combination can be formulated as a controlled or sustained release oral formulation in any suitable tablet, coated tablet or multiparticulate formulation known to those skilled in the art. The sustained release dosage form may optionally include a sustained released carrier which is incorporated into a matrix along with the opiate, or which is applied as a sustained release coating.

The sustained release dosage form may include the μ-opiate analgesic in sustained release form and the NMDA antagonist and capsaicin or an ester of capsaicin in sustained release form or in immediate release form. The NMDA antagonist and capsaicin or an ester of capsaicin may be incorporated into the sustained release matrix along with the opiate, incorporated into the sustained release coating; incorporated as a separated sustained release layer or immediate release layer, or may be incorporated as a powder, granulation, etc., in a gelatin capsule with the substrates of the present invention. Alternatively, the sustained release dosage form may have the NMDA antagonist in sustained release form and the μ-opiate analgesic and capsaicin or an ester of capsaicin in sustained release form or immediate release form.

An oral dosage form according to the invention may be provided as, for example, granules, spheroids, beads, and pellets or pills. These formulations are hereinafter collectively referred to as "multiparticulates" and/or particles. An amount of the multiparticulates that is effective to provide the desired dose of opiate over time may be placed in a capsule or may be incorporated in any other suitable oral solid form.

In one preferred embodiment of the present invention, the sustained release dosage form comprises such particles containing or comprising the active ingredient, wherein the particles have diameter from about 0.1 mm to about 2.5 mm, preferably from about 0.5 mm to about 2 mm.

In certain embodiments, the particles comprise normal release matrixes containing the μ-opiate analgesic with or without the NMDA antagonist and capsaicin or an ester of capsaicin. These particles are then coated with the sustained release carrier. In embodiments where the NMDA antagonist and capsaicin or an ester of capsaicin are immediately released, the NMDA antagonist and capsaicin or an ester of capsaicin may be included in separate normal release matrix particles, or may be co-administered in a different immediate release composition which is either enveloped within a gelatin capsule or is administered separately. In other embodiments, the particles comprise inert beads that are coated with the opiate analgesic with or without the NMDA antagonist and capsaicin or an ester of capsaicin. Thereafter, a coating comprising the sustained release carrier is applied onto the beads as an overcoat.

The particles are preferably film coated with a material that permits release of the opiate or its salt, and if desired, the NMDA antagonist and capsaicin or an ester of capsaicin at a sustained rate in an aqueous medium. The film coat is chosen so as to achieve, in combination with the other stated properties, a desired in vivo release rate. The sustained release coating formulations of the present invention should be capable of producing a strong, continuous film that is smooth and elegant, capable of supporting pigments and other coating additives, non-toxic, inert, and tack free.

Coatings

The dosage forms of the present invention may optionally be coated with one or more materials suitable for the regulation of release or for the protection of the formulation. In one embodiment, coatings are provided to permit either pH dependent or pH independent release, e.g., when exposed to gastrointestinal fluid. A pH dependent coating serves to release the opiate in desired areas of the gastro-intestinal (GI)

tract, e.g., the stomach or small intestine, such that an absorption profile is provided which is capable of providing at least about twelve hour and preferably up to twenty four hour analgesia to a patient. When a pH independent coating is desired, the coating is designed to achieve optimal release regardless of pH changes in the environmental fluid, e.g., the GI tract. It is also possible to formulate compositions which release a portion of the dose in one desired area of the GI tract, e.g., the stomach, and release the remainder of the dose in another area of the GI tract, e.g., the small intestine.

Formulations according to the invention that utilize pH dependent coatings to obtain formulations may also impart a repeat-action or pulsatile release effect whereby unprotected drug is coated over the enteric coat and is released in the stomach, while the remainder, being protected by the enteric coating, is released further down the gastrointestinal tract. Coatings which are pH dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the μ-opiate analgesic (with or without the NMDA antagonist and capsaicin or an ester of capsaicin) is coated with a hydrophobic material selected from (i) an alkylcellulose; (ii) an acrylic polymer, or (iii) mixtures thereof. The coating may be applied in the form of an organic or aqueous solution or dispersion. The coating may be applied to obtain a weight gain from about 2 to about 25% of the substrate in order to obtain a desired sustained release profile. Such formulations are described in detail in U.S. Pat. Nos. 5,273,760 and 5,286,493, assigned to the Assignee of the present invention and hereby incorporated by reference in their entirety.

Other examples of sustained release formulations and coatings that may be used in accordance with the present invention include Assignee's U.S. Pat. Nos. 5,324,351, 5,356,467, and 5,472,712, hereby incorporated by reference in their entirety.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

One commercially available aqueous dispersion of ethylcellulose is sold as Aquacoat™ (FMC Corp., Philadelphia, Pa., U.S.A.). Aquacoat™ is prepared by dissolving the ethylcellulose in a water immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudo-latex during the manufacturing phase. Thus, prior to using the same as a coating, it is necessary to intimately mix the Aquacoat™ with a suitable plasticizer prior to use.

Another aqueous dispersion of ethylcellulose is commercially available as Surelease™ (Colorcon, Inc., West Point, Pa., U.S.A.). This product is prepared by incorporating plasticizer into the dispersion during the manufacturing process. A hot melt of a polymer containing for example a plasticizer such as dibutyl sebacate, and a stabilizer such as oleic acid is prepared as a homogeneous mixture, which is then diluted with an alkaline solution to obtain an aqueous dispersion which can be applied directly onto substrates.

Acrylic Polymers

In other preferred embodiments of the present invention, the hydrophobic material comprising the controlled release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral methacrylic esters.

Certain methacrylic acid ester type polymers are useful for preparing pH dependent coatings that may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit™ from Rohm Tech, Inc. There are several different types of Eudragit™. For example Eudragit™ E is an example of a methacrylic acid copolymer that swells and dissolves in acidic media. Eudragit™ L is a methacrylic acid copolymer which does not swell at about pH<5.7 and is soluble at about pH>6. Eudragit™ S does not swell at about pH<6.5 and is soluble at about pH>7. Eudragit™ L and Eudrag it S are water swellable, and the amount of water absorbed by these polymers is pH dependent. However, dosage forms coated with Eudragit™ L and S are pH independent.

In certain preferred embodiments, the acrylic coating comprises a mixture of two acrylic resin lacquers commercially available from Rohm Pharma under the Tradenames Eudragit™ L30D and Eudrag it S30D, respectively. Eudragit™ L30D and Eudragit™ S30D are copolymers of acrylic and methacrylic esters with a low content of quaternary ammonium groups, the molar ratio of ammonium groups to the remaining neutral methacrylic esters being 1:20 in Eudragit™ L30D and 1:40 in Eudragit™ S30D. The mean molecular weight is about 150,000. The code designations RL (high permeability) and RS (low permeability) refer to the permeability properties of these agents. Eudragit™ RL/RS mixtures are insoluble in water and in digestive fluids. However, coatings formed from the same are swellable and permeable in aqueous solutions and digestive fluids.

The Eudragit™ RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit™ RL, 50% Eudrag it RL and 50% Eudragit™ RS, and 10% Eudragit™ RL Eudrag it 90%

RS. Of course, one skilled in the art will recognize that other acrylic polymers may also be used, such as, for example, Eudragit™ L.

Plasticizers

In embodiments of the present invention where the coating comprises an aqueous dispersion of a hydrophobic material, the inclusion of an effective amount of a plasticizer in the aqueous dispersion of hydrophobic material will further improve the physical properties of the sustained release coating. For example, because ethylcellulose has a relatively high glass transition temperature and does not form flexible films under normal coating conditions, it is preferable to incorporate a plasticizer into an ethylcellulose coating containing sustained release coating before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers, such as acetylated monoglycerides, phthalate esters, castor oil, etc., may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers that have proved to be suitable for enhancing the elasticity of the films formed from acrylic films such as Eudragit™ RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

Processes for Preparing Coated Beads

When the aqueous dispersion of hydrophobic material is used to coat inert pharmaceutical beads such as nu-pariel 18/20 beads, a plurality of the resultant stabilized solid controlled release beads may thereafter be placed in a gelatin capsule in an amount sufficient to provide an effective controlled release dose when ingested and contacted by an environmental fluid, e.g., gastric fluid or dissolution media.

The stabilized controlled release bead formulations of the present invention slowly release the therapeutically active agent, e.g., when ingested and exposed to gastric fluids, and then to intestinal fluids. The controlled release profile of the formulations of the invention can be altered, for example, by varying the amount of overcoating with the aqueous dispersion of hydrophobic material, altering the manner in which the plasticizer is added to the aqueous dispersion of hydrophobic material, by varying the amount of plasticizer relative to hydrophobic material, by the inclusion of additional ingredients or excipients, by altering the method of manufacture, etc. The payload release profile of the product may also be modified by increasing or decreasing the thickness of the retardant coating.

Spheroids or beads coated with a therapeutically active agent are prepared, e.g., by dissolving the therapeutically active agent in water and then spraying the solution onto a substrate, for example, nu pariel 18/20 beads, using a Wuster insert. Optionally, additional ingredients are also added prior to coating the beads in order to assist the binding of the opiate to the beads, and/or to color the solution, etc. For example, a product that includes hydroxypropylmethylcellulose, etc. with or without a colorant, such as Opadry™, commercially available from Colorcon, Inc., may be added to the solution and the solution mixed for about 1 hour prior to application of the same onto the beads. The resultant coated substrate, in this example beads, may then be optionally overcoated with a barrier agent, to separate the therapeutically active agent from the hydrophobic controlled release coating. An example of a suitable barrier agent is one that comprises hydroxypropylmethylcellulose. However, any film former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticizer, e.g. triethyl citrate. Pre-formulated aqueous dispersions of ethylcellulose, such as Aquacoat™ or Surelease™, may be used. If Surelease™ is used, it is not necessary to separately add a plasticizer. Alternatively, pre-formulated aqueous dispersions of acrylic polymers such as Eudragit™ can be used.

The coating solutions of the present invention preferably contain, in addition to the film former, plasticizer, and solvent system such as water and a colorant to provide elegance and product distinction. Color may be added to the solution of the therapeutically active agent instead, or in addition to the aqueous dispersion of hydrophobic material. For example, color be added to Aquacoat™ via the use of alcohol or propylene glycol based color dispersions, milled aluminum lakes and opacifiers such as titanium dioxide by adding color with shear to water soluble polymer-solution and then using low shear to the plasticized Aquacoat™. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the release retarding effect of the coating.

The plasticized aqueous dispersion of hydrophobic material may be applied onto the substrate comprising the therapeutically active agent by spraying using any suitable spray equipment known in the art. In a preferred method, a Wurster fluidized bed system is used in which an air jet, injected from underneath, fluidizes the core material and effects drying while the acrylic polymer coating is sprayed on. A sufficient amount of the aqueous dispersion of hydrophobic material to obtain a predetermined controlled release of said therapeutically active agent when said coated substrate is exposed to aqueous solutions, such as gastric fluid, is preferably applied, taking into account the physical characteristics of the therapeutically active agent, the manner of incorporation of the plasticizer, etc. After coating with the hydrophobic material, a further overcoat of a film-former, such as Opadry™, is optionally applied to the beads. This overcoat is provided, if at all, in order to substantially reduce agglomeration of the beads.

The release of the therapeutically active agent from the controlled release formulation of the present invention can be further influenced and adjusted to a desired rate by the addition of one or more release modifying agents. Controlled release may be achieved in the alternative by providing one or more passageways through the coating through which the drug or a solution of the drug can diffuse. The ratio of hydrophobic material to water soluble material is determined by, among other factors, the release rate required to produce the desired therapeutic effect and the solubility characteristics of the materials selected.

The release modifying agents which function as pore formers may be organic or inorganic, and include materials that can be dissolved, extracted or leached from the coating in the environment of use. The pore-formers may comprise one or more hydrophilic materials such as hydroxypropylmethylcellulose.

The sustained release coatings of the present invention can also include erosion promoting agents such as starches and gums.

The sustained release coatings of the present invention can also include materials useful for making microporous lamina in the environment of use, such as polycarbonates comprised of linear polyesters of carbonic acid in which carbonate groups reoccur in the polymer chain. The release modifying agent may also comprise a semi-permeable polymer.

In certain preferred embodiments, the release modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. Nos. 3,845,770, 3,916,889, 4,063,064 and 4,088,864, all of which are hereby incorporated by reference. The passageway can have any shape such as round, triangular, square, elliptical, irregular, etc.

Matrix Bead Formulations

In other embodiments of the present invention, the controlled release formulation is achieved via a matrix having a controlled release coating as set forth above. The present invention may also utilize a controlled release matrix that affords in vitro dissolution rates of the opiate within the preferred ranges and that releases the opiate in a pH dependent or pH independent manner. The materials suitable for inclusion in a controlled release matrix will depend on the method used to form the matrix.

For example, a matrix in addition to the µ-opiate analgesic and, optionally, a NMDA antagonist and capsaicin or an ester of capsaicin may include:

Hydrophilic and/or hydrophobic materials, such as gums, cellulose ethers, acrylic resins, protein derived materials; the list is not meant to be exclusive, and any pharmaceutically acceptable hydrophobic material or hydrophilic material which is capable of imparting controlled release of the active agent and which melts or softens to the extent necessary to be extruded may be used in accordance with the present invention.

Digestible, long chain ($C_8$ to $C_{50}$, especially $C_{12}$ to $C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols.

Of these polymers, acrylic polymers, especially Eudragit™, RSPO, the cellulose ethers, especially hydroxyalkylcelluloses and carboxyalkylceluloses, are preferred. The oral dosage form may contain between 1% and 80% by weight of at least one hydrophilic or hydrophobic material.

When the hydrophobic material is a hydrocarbon, the hydrocarbon preferably has a melting point of between 25 and 90 carbon atoms. Of the long chain hydrocarbon materials, fatty aliphatic alcohols are preferred. The oral dosage form may contain up to 60% (by weight) of at least one digestible, long chain hydrocarbon.

Preferably, the oral dosage form contains up to 60% by weight of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, polyacrylic acid, polymethacrylic acid, methacrylic acid alkylamine copolymer, polymethyl methacrylate, polymethacrylic acid anhydride, polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 30 to about 200° C., preferably from about 45 to about 90° C. Specifically, the hydrophobic material may comprise natural or synthetic waxes, fatty alcohols such as lauryl, myristyl, stearyl, cetyl or preferably cetostearyl alcohol, fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For purposes of the present invention, a wax-like substance is defined as any material that is normally solid at room temperature and has a melting point of from about 30 to about 100° C.

Suitable hydrophobic materials which may be used in accordance with the present invention include digestible, long chain ($C_8$ to $C_{50}$, especially $C_{12}$ to $C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25 and 90° C. are preferred. Of the long chain hydrocarbon materials, fatty (aliphatic) alcohols are preferred in certain embodiments. The oral dosage form may contain up to 60% by weight of at least one digestible, long chain hydrocarbon.

Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$ to $C_{36}$, preferably $C_{14}$ to $C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and, especially, hydroxyethylcellulose. The amount of the at least one hydroxyalkyl cellulose in the present oral dosage form will be determined, inter alia, by the precise rate of opiate release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opiate release required. It will also depend on whether at least one polyalkylene glycol is present in or absent from the oral dosage form. In the absence of at least one polyalkylene glycol, the oral dosage form preferably contains between 20% and 50% by weight of the at least one aliphatic alcohol. When at least one polyalkylene glycol is present in the oral dosage form, then the combined weight of the at least one aliphatic alcohol and the at least one polyalkylene glycol preferably constitutes between 20% and 50% by weight of the total dosage.

In one embodiment, the ratio of hydroxyalkyl cellulose or acrylic resin to the aliphatic alcohol/polyalkylene glycol determines, to a considerable extent, the release rate of the opiate from the formulation. A ratio of the hydroxyalkyl cellulose to the aliphatic alcohol/polyalkylene glycol of between 1:2 and 1:4 is preferred, with a ratio of between 1:3 and 1:4 being particularly preferred.

The polyalkylene glycol may be, for example, polypropylene glycol or, which is preferred, polyethylene glycol. The number average molecular weight of the polyalkylene glycol is preferred between 1,000 and 15,000 especially between 1,500 and 12,000.

Another suitable controlled release matrix would comprise an alkylcellulose, especially ethyl cellulose, a $C_{12}$ to $C_{36}$ aliphatic alcohol and optionally a polyalkylene glycol.

In another preferred embodiment the matrix includes a pharmaceutically acceptable combination of at least two hydrophobic materials.

In addition to the above ingredients a controlled release matrix may also contain suitable quantities of other materials, for example diluents, lubricants, binders, granulating aids, colorants, flavorants and glidants that are conventionally used in the art of pharmaceutical formulation.

Processes for Preparing Matrix Based Beads

In order to facilitate the preparation of a solid, controlled release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose and opiate or an opiate salt; (b) mixing the hydroxyalkyl cellulose containing granules with at least one $C_{12}$ to $C_{36}$ aliphatic alcohol; and (c) optionally, compressing and shaping the granules. Preferably, the granules are formed by wet granulating the hydroxyalkyl cellulose/opiate with water. In a particularly preferred embodiment of this process, the amount of water added during tie wet granulation step is preferably between 1.5 and 5 times, especially between 1.75 and 3.5 times, the dry weight of the opiate.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101™ (FMC Corporation). In such embodiments, in addition to the active ingredient and spheronizing agent, the spheroids may also contain a binder. Suitable binders, such as low viscosity water soluble polymers, will be well known to those skilled in the pharmaceutical arts. However water soluble hydroxy lower alkyl cellulose, such as hydroxypropylcellulose are preferred. Additionally, or alternatively, the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol, or (b) shellac or zein.

Melt Extrusion Matrix

Sustained release matrices can also be prepared via melt-granulation or melt-extrusion techniques. Generally, melt-granulation techniques involve melting a normally solid hydrophobic material, such as a wax, and incorporating a powdered drug therein. To obtain a sustained release dosage form, it may be necessary to incorporate an additional hydrophobic substance, such as ethylcellulose or a water insoluble acrylic polymer, into the molten wax hydrophobic material. Examples of sustained release formulations prepared by melt granulation techniques as are found in U.S. Pat. No. 4,861,598, assigned to the Assignee of the present invention and hereby incorporated by reference in its entirety.

The additional hydrophobic material may comprise one or more water-insoluble wax like thermoplastic substances possibly mixed with one or more wax like thermoplastic substances being less hydrophobic than said one or more water insoluble wax like substances. In order to achieve constant release, the individual wax like substances in the formulation should be substantially non-degradable and insoluble in gastrointestinal fluids during the initial release phases. Useful water-insoluble wax like substances may be those with a water solubility that is lower than about 1:5,000 (w/w).

In addition to the above ingredients, a sustained release matrix may also contain suitable quantities of other materials, such as diluents, lubricants, binders, granulating aids, colorants, flavorants and glidants that are conventionally used in the pharmaceutical arts. The quantities of these additional materials will be sufficient to provide the desired effect to the desired formulation. In addition to the above ingredients, a sustained release matrix incorporating melt-extruded multiparticulates may also contain suitable quantities of other materials, such as diluents, lubricants, binders, granulating aids, colorants, flavorants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986), incorporated by reference herein.

Melt Extrusion Multiparticulates

The preparation of a suitable melt-extruded matrix according to the present invention may, for example, include the steps of blending the opiate analgesic, together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 to about 5 mm and provides sustained release of the therapeutically active agent for a time period of from about 8 to about 24 hours.

An optional process for preparing the melt extrusions of the present invention includes directly metering into an extruder a hydrophobic material, a therapeutically active agent, and an optional binder, heating the homogenous mixture; extruding the homogenous mixture to thereby form strands; cooling the strands containing the homogeneous mixture, cutting the strands into particles having a size from about 0.1 mm to about 12 mm, and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 to about 12 mm in length and have a diameter of from about 0.1 to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tableting equipment using standard techniques. Techniques and compositions for making tablets that are compressed and/or molded, capsules of hard and soft gelatin, and pills are also described in Remington's Pharmaceutical Sciences, (Arthur Osol, editor), 1553-1593 (1980), incorporated by reference herein.

In yet another preferred embodiment, the extrudate can be shaped into tablets as set forth in U.S. Pat. No. 4,957,681, (Klimesch, et al), described in additional detail above and hereby incorporated by reference.

Optionally, the sustained release melt-extruded multiparticulate systems or tablets can be coated, or the gelatin capsule can be further coated, with a sustained release coating such as the sustained release coatings described above. Such coatings preferably include a sufficient amount of hydrophobic material to obtain a weight gain level from about 2 to about 30 percent, although the overcoat may be greater depending upon the physical properties of the particular opiate analgesic compound utilized and the desired release rate, among other things.

The melt extruded unit dosage forms of the present invention may further include combinations of melt extruded multiparticulates containing one or more of the therapeutically active agents disclosed above before being encapsulated. Furthermore, the unit dosage forms can also include an amount of an immediate release therapeutically active agent for prompt therapeutic effect. The immediate release therapeutically active agent may be incorporated as separate pellets within a gelatin capsule, or may be coated on the surface of the multiparticulates after preparation of the dosage forms such as within a controlled release coating or matrix base. The unit dosage forms of the present invention may also contain a combination of controlled release beads and matrix multiparticulates to achieve a desired effect.

The sustained release formulations of the present invention preferably slowly release the therapeutically active agent, such that when the dosage form is ingested and exposed to gastric fluids, and then to intestinal fluids a therapeutically desirable plasma level is obtained. The sustained release profile of the melt extruded formulations of the invention can be altered, for example, by varying the amount of retardant which may be a hydrophobic material, by varying the amount of plasticizer relative to hydrophobic material, by the inclusion of additional ingredients or excipients, or by altering the method of manufacture, etc.

In other embodiments of the invention, the melt extruded material is prepared without the inclusion of the therapeutically active agent, which is added thereafter to the extrudate. Such formulations typically will have the therapeutically active agent blended together with the extruded matrix material, and then the mixture would be tableted in order to provide a slow release formulation. Such formulations may be advantageous, for example, when the therapeutically active agent included in the formulation is sensitive to temperatures needed for softening the hydrophobic material and/or the retardant material.

The following examples illustrate various aspects of the present invention. They are not to be construed to limit the sentences in any manner whatsoever.

EXAMPLE 1

Preparation of butyryl ester of Capsaicin USP27 (Formula I, $R=C_3H_7$)

A mixture of 30.5 gm (~0.1M) of capsaicin USP27 (HUBEI XIANGXI CHEMICAL INDUSTRY CO., LTD, China), 16.7 ml (0.12M) of anhydrous triethylamine (Spectrum Chemicals) and 200 ml of anhydrous dichloromethane was placed into a 1000 ml 2-neck round bottomed flask. The content was covered with aluminum foil to protect it from light exposure. The flask was fitted with a condenser fitted with a moisture trap on the top and a dropwise addition funnel. The flask was kept at room temperature and 10.6 ml (0.1M) of butyryl chloride was added from the funnel into the mixture slowly with stirring. After the addition, the mixture was refluxed at 45 degree C. for 6-8 hours and stirred for another 18-24 hours at room temperature. The mixture was transferred into a separating funnel and washed successively with 2×500 ml of water, 2×500 ml of dilute hydrochloric acid, 2×500 ml of 10% sodium bicarbonate solution and 3×500 ml of type I water. The organic layer was separated, dried with anhydrous magnesium sulfate and the dichloromethane was removed under vacuum to produce a clear, yellow viscous oil (95% of theoretical).

EXAMPLE 2

Preparation of hexanoyl ester of Capsaicin USP27
(Formula I, R=CH$_3$—(CH$_2$)$_4$)

The compound was prepared essentially as described in Example 1, using n-hexanoyl chloride instead of butyryl chloride. The product was recovered as a low melting viscous yellow oil.

EXAMPLE 3

Preparation of palmitoyl ester of Capsaicin USP27
(Formula I, R=CH$_3$—(CH$_2$)$_{14}$)

The compound was prepared essentially as described in Example 1, using n-palmitoyl chloride instead of butyryl chloride. The product was recovered as a waxy yellow solid.

EXAMPLE 4

Capsule Formulation

The following ingredients in each one of the capsule formulations were weighed accurately, ground using a pestle and mortar to fine and homogeneous powders. These powders were sieved through 100 mesh and filled into hard gelatin capsules. The composition of each capsule formulation is listed below.

Capsule Formulation 1

|  | In each | In 100 |
|---|---|---|
| Tramadol Hydrochloride | 39.8 mg | 4.00 g |
| Dextromethorphan Hydrochloride | 51.0 mg | 5.10 g |
| Capsaicin Palmitate | 5.4 mg | 0.54 g |
| Ascorbyl Palmitate | 20.0 mg | 2.00 g |
| Microcrystalline Cellulose | 90.8 mg | 9.08 g |
| Sodium Lauryl Sulfate | 1.5 mg | 0.15 g |
| Silicon dioxide | 1.5 mg | 0.15 g |
| Total Solid | 210 mg | 21.0 g |

Capsule Formulation 2

|  | In each | In 100 |
|---|---|---|
| Tramadol Hydrochloride | 39.8 mg | 3.98 g |
| Dextromethorphan Hydrochloride | 51.0 mg | 5.10 g |
| Capsaicin Palmitate | 10.8 mg | 1.08 g |
| Ascorbyl Palmitate | 20.0 mg | 2.00 g |
| Microcrystalline Cellulose | 60.4 mg | 6.04 g |
| Lactose | 25.0 mg | 2.50 g |
| Sodium Lauryl Sulfate | 1.5 mg | 0.15 g |
| Silicon dioxide | 1.5 mg | 0.15 g |
| Total Solid | 210 mg | 21.0 g |

Capsule Formulation 3

|  | In each | In 100 |
|---|---|---|
| Tramadol Hydrochloride | 35.0 mg | 3.50 g |
| Dextromethorphan Hydrochloride | 45.0 mg | 4.50 g |
| Capsaicin Palmitate | 11.2 mg | 1.12 g |
| Ascorbyl Palmitate | 25.0 mg | 2.50 g |
| Microcrystalline Cellulose | 65.8 mg | 6.58 g |
| Lactose | 25.0 mg | 2.50 g |
| Sodium Lauryl Sulfate | 2.0 mg | 0.20 g |
| Silicon dioxide | 1.0 mg | 0.10 g |
| Total Solid | 210 mg | 21.0 g |

Capsule Formulation 4

|  | In each | In 100 |
|---|---|---|
| Tramadol Hydrochloride | 50.0 mg | 5.00 g |
| Dextromethorphan Hydrochloride | 30.0 mg | 3.00 g |
| Capsaicin Palmitate | 11.2 mg | 1.12 g |
| Ascorbyl Palmitate | 25.0 mg | 2.50 g |
| Microcrystalline Cellulose | 65.8 mg | 6.58 g |
| Lactose | 25.0 mg | 2.50 g |
| Sodium Lauryl Sulfate | 2.0 mg | 0.20 g |
| Silicon dioxide | 1.0 mg | 0.10 g |
| Total Solid | 210 mg | 21.0 g |

Capsule Formulation 5

|  | In each | In 100 |
|---|---|---|
| Tramadol Hydrochloride | 40.0 mg | 4.00 g |
| Dextromethorphan Hydrochloride | 51.0 mg | 5.10 g |
| Capsaicin USP | 3.0 mg | 0.30 g |
| Ascorbyl Palmitate | 25.0 mg | 2.50 g |
| Microcrystalline Cellulose | 58.0 mg | 5.80 g |
| Lactose | 30.0 mg | 3.00 g |
| Sodium Lauryl Sulfate | 2.0 mg | 0.20 g |
| Silicon dioxide | 1.0 mg | 0.10 g |
| Total Solid | 210 mg | 21.0 g |

EXAMPLE 5

Treatment of Pain with the Composition of the Present Invention and the Topical Formulation of Butyryl capsaicin USP27

Case I. Patient with Diabetic Neuropathy in the Feet

A 53 year old hispanic male has developed Type 2 diabetes a year ago and has diabetic neuropathy in the feet. He was given the capsules of composition 1 in example 4 and a 0.5% butyryl-capsaicin USP27 gel and the following is his testimony on the effectiveness of the oil for the treatment of cold sores. "I was diagnosed with type 2 diabetes last year. I also have neuropathy in my feet. I had an ulcer on my foot and was treated by a local pediatric doctor in San Antonio. My ulcer has since been cleared up. I control my diabetic ailment with a low-carb diet only, with no medication. I have also lost 40 lbs. since my diagnosis last year. I however feel pain on the bottom of my feet at times. Since taking the cream by application on my feet, I have noticed much less discomfort than usual. The comfort that I noticed has lasted up to 24 hrs per-application. In addition, I started taking 1 capsules every 12 to 24 hours to further reduce my pain. I noticed that within a day, the pain is almost gone and I can sleep well during the night. This cream and the capsules really help my condition and would like to let your research company to know about your product".

Case II. Patient with Severe Diabetic Neuropathy

A 40 year old female developed diabetic neuropathy in 2000 and was given capsules of composition 1 in example 4 and 0.5% butyryl capsaicin cream for treating her pain in the feet. She gave the following testimony about the treatment. "I was diagnosed with neuropathy in 2000. There never has been much they could do for me other than give me pain medication that's addictive. At this time, I'm on Neurontin 1800 mg a day, Vicodin 5-6 tablets a day. Diclofenac 150 mg a day, and also get injections in my feet. In the last 7 months I have had 5 different cast on my left foot. Since my left foot has a cast my right foot has become worse because all of my weight has been on my right foot. I used the creme and within 30 min. I could feel the difference. Later I was up walking and realized there was no pain at all. I started taking the capsule 1-2 a day in addition to the topical cream. At night I don't sleep well because of the pain, but I was able to go to sleep the whole night through without cramps and pain. My cast was removed in few days and now I am applying the 0.5% cream on both of my feet once every day and take 1-2 capsules a day. I have experienced excellent results and I am almost completely free of any pain now. I am no longer taking my prescribed pain medication for the past two weeks".

Case III. Patient with Pinched Nerve Pain

A 65 year old female developed pain due to pinched nerve and was given the 0.5% butyryl capsaicin USP27 gel and the capsules of composition 1 in example 4. She gave the following testimony about the treatment. "Over a period of years, periodically a pinched nerve would occur in the left lower side of my back. This required chiropractic treatment which at times was not always successful requiring several additional treatments. After using the cream, my pain has disappeared and that was three days ago and still no pain. Now I am taking one capsule a day whenever I feel the pain along with the cream and I am completely free of pain now".

Case IV. Patient with Severe Diabetic Neuropathy

A 49 year old male developed diabetic neuropathy in 2001 and was given 0.5% butyryl capsaicin USP27 gel and the capsules of composition 1 in example 4 for treating his pain in the feet. He gave the following testimony about the treatment. "I have diabetic neuropathy brought on by extreme intravenous application of antibiotics for a six day period. Since that time I have experienced unmanageable pain causing sleep depravation, anxiety with no relief on the market. Prescriptions for anti-depressants were given by my personal physician but to no avail. Now with this cream I can sleep without any disturbances. Nothing on the market today could help me without the use of addicting narcotics that were marginally effective at best. Now I am also taking one capsule a day along with the cream and the pain is almost gone".

Case V. Patient with Severe Neuropathy

A 62 year old female developed neuropathy in 1975 and was given 0.5% butyryl capsaicin USP27 gel and capsules of composition I in example 4 for treating her pain in the feet. She gave the following testimony about the treatment. "My neuropathy numbness in feet and hands first started after back surgery in 1975 my L 4 and 5 were fused and some disks removed. The numbness and pain increased after surgery for a double mastectomy which was botched by a Doctor inexperienced at this surgery in 1988 causing sever pain in my abdominal muscles and up my chest. In 1992 I was in the hospital for depression a new Doctor prescribed Percocet medication for my pain. The Percocet helped but I had to take 8 a day 5/325 mgs with anti depression medication at the time. The pain was so overwhelming after 4 years that I decided one day to end it all and I was found by my husband on the floor. I had kept my pain a secret over the 4 years hoping it would just eventually go away and I had never told my family that I was suffering so much. I had overdosed with the Percocet in an attempt to end my pain for good. I recovered some and I tried to cut back on the Percocet and got down to 1 a day to prevent addiction. The increase in pain and numbness was causing me to stumble when I walked. A neurologist in 1998 suggested that I try Neurontin which is used for epilepsy. I think I was taking 100 mgs 3 times a day at first then increased in 6 weeks to 200 mgs 3 times a day, when that failed we went up to 300 mgs 3 times a day. The 300 mgs was starting to help some but they had to increase to 800 mgs 5 times a day to really help my pain. This helped more than the Percocet alone but I still needed to keep the Percocet at reduced amounts. I fell and broke my back fusion in 2000. New back surgery attempted to fuse my back again but in 2003 doctors had to use rods and pins to secure it. With each surgery my numbness and pain would increase. I tried water therapy and various physical therapies but nothing could relieve my pain. I have had other injuries as well, in 2002 a broken right ankle and compression fracture in my right knee and in 2003 I broke my left ankle. In October 2005 a Doctor specializing in neurological disorders said the Neurontin was probably weakening my bones and switched me to a generic version of the same medication and dropped the dose to 50 mgs a day. My pain increased immediately and I went through withdrawals with the smaller dose. This Doctor said if the pain didn't decrease I was to increase one tablet more a day each week till the end of the $4^{th}$ week and return to him. I never went back to this Doctor and just increased back to 800 mgs 5 times a day to coupe with the pain, burning, and itching feelings. I had to take depression medication again at this time. I tried a new topical cream just this week Jul. 11, 2006 being developed in San Antonio, Tex. One of my most disruptive symptoms in my feet would cause me to involuntarily jump in bed and I was beginning to feel this come on when I applied the cream to my left foot. The symptoms just stopped! Usually this symptom would last several hours to even days. I have burning sensations in both hands and up my forearm but after applying this cream I had my first relief from that burning feeling since my back surgeries in 2003! This cream has done more to relieve my symptoms than both Percocet and Neurontin has ever done for me! I now have renewed hope to stop taking all this internal medication that is bound to hurt my liver and is weakening my bones. After seeing the remarkable result, now I am also taking 1-2 capsules a day and my pain is totally eliminated".

Case VI. Patient with Severe Back Pain

A 52 year old male developed back pain almost 25 years ago due to a car accident. The accident caused a compression of the mid portion of his spine. He was given 0.5% butyryl capsaicin USP27 gel and capsules of composition 1 in example 4 for treating his chronic back pain. He gave the following testimony about the treatment. "I am in the catering industry as the principle of my company, I have to do lot of physical labor and towards the end of the evening I am fatigued and in tremendous pain. In the scale of 1 to 10, my pain is a 10. I started taking 1-2 capsules a day and within 45 minutes my pain is a 1 on the 10 scale. I can do my work and return home and enjoy a good night sleep. Thanks so much for the pain relief".

We claim:

1. An analgesic pharmaceutical composition consisting essentially of: a) dextromethorphan, b) an ester of capsaicin and c) a μ-opiate analgesic that is tramadol or a pharmaceutically acceptable salt or complex thereof, and a pharmaceutically acceptable excipient.

2. The analgesic pharmaceutical composition of claim 1, wherein the ester of capsaicin is of formula (I):

wherein CAP is capsaicin, civamide, homocapsaicin, nordihydrocapsaicin, dihydrocapsaicin, homodihydrocapsaicin, n-vanillyloctanamide, nonivamide and n-vanillyldecanamide; wherein R is selected from alkyl groups of up to 22 carbon atoms and aryl groups of up to 22 carbon atoms and alkylene group of up to 22 carbon atoms and an arylene group of up to 22 carbon atoms.

3. The analgesic pharmaceutical composition of claim 2, wherein R is selected from the group consisting of: methyl, ethyl, propyl, butyl, hexyl, heptyl, octyl, dodecyl, 1-pentadecyl, 1-heptadecyl, isopropyl, sec-butyl, t-butyl, 2-methylbutyl, 2-pentyl, 3-pentyl, cyclopropyl, cyclobutyl, cyclopentyl, cyclohexyl, vinyl (ethenyl), 1-propenyl, i-butenyl, pentenyl, hexenyl, n-decenyl, —CH2—CH2—COOH and c-pentenyl groups.

4. The analgesic pharmaceutical composition of claim 3, wherein the ester of capsaicin is capsaicin palmitate.

5. The analgesic pharmaceutical composition of claim 4, wherein the composition consists of dextromethorphan, capsaicin palmitate and tramadol, and a pharmaceutically acceptable excipient.

6. The analgesic pharmaceutical composition of claim 1, in a dosage form selected from the group consisting of a tablet, a multiparticulate formulation for oral administration; a solution, a sustained release formulation, a suspension or elixir for oral administration, an injectable formulation, an implantable device, a topical preparation, a solid state and or depot type transdermal delivery device(s), a suppository, a buccal tablet, and an inhalation formulation.

7. The analgesic pharmaceutical composition of claim 6, further defined as a solid oral dosage form formulated as a tablet or capsule.

8. The analgesic pharmaceutical composition according to claim 1, wherein the ratio of dextromethorphan to μ-opiate analgesic is from about 15:1 to 1:15.

9. The analgesic pharmaceutical composition of claim 8, wherein the ratio of dextromethorphan to μ-opiate analgesic is from about 10:1 to 1:10.

10. The analgesic pharmaceutical composition of claim 9, wherein the ratio of dextromethorphan to μ-opiate analgesic is from about 5:1 to 1:5.

11. The analgesic pharmaceutical composition of claim 10, wherein the ratio of dextromethorphan to μ-opiate analgesic is about 1:2.

12. The analgesic pharmaceutical composition of claim 1, wherein the ratio of dextromethorphan to an ester of capsaicin to μ-opiate analgesic is from about 90:1:1 to 1:90:1 to 1:1:90.

13. The analgesic pharmaceutical composition of claim 1, in a dosage form selected from the group consisting of a tablet, a multiparticulate formulation for oral administration; a solution, a sustained release formulation, a suspension or elixir for oral administration, an injectable formulation, an implantable device, a topical preparation, a solid state and or depot type transdermal delivery device(s), a suppository, a buccal tablet, and an inhalation formulation such as a controlled release particle formulation or spray, mist or other topical vehicle, intended to be inhaled or instilled into the sinuses.

14. The analgesic pharmaceutical composition of claim 13, further defined as a solid oral dosage form formulated as a tablet or capsule.

15. The analgesic pharmaceutical composition of claim 2, wherein R is a substituted alkyl, aryl or alkylene groups.

16. The analgesic pharmaceutical composition of claim 2, wherein R is a branched or straight chained alkyl, aryl, or alkylene group.

17. The analgesic pharmaceutical composition of claim 2, wherein R is a straight chained or branched alkyl.

18. The analgesic pharmaceutical composition of claim 1, wherein the ester of capsaicin is capsaicin palmitate.

* * * * *